US011433042B2

(12) United States Patent
Tseng et al.

(10) Patent No.: US 11,433,042 B2
(45) Date of Patent: Sep. 6, 2022

(54) METHODS AND COMPOSITIONS FOR TREATING METABOLIC DISORDERS

(71) Applicant: Joslin Diabetes Center, Inc., Boston, MA (US)

(72) Inventors: Yu-Hua Tseng, Newton, MA (US); Matthew Lynes, Brookline, MA (US)

(73) Assignee: Joslin Diabetes Center, Inc., Boston, MA (US)

( * ) Notice: Subject to any disclaimer, the term of this patent is extended or adjusted under 35 U.S.C. 154(b) by 221 days.

(21) Appl. No.: 16/532,114

(22) Filed: Aug. 5, 2019

(65) Prior Publication Data

US 2020/0022940 A1 Jan. 23, 2020

Related U.S. Application Data

(63) Continuation of application No. PCT/IB2018/050744, filed on Feb. 6, 2018.

(60) Provisional application No. 62/455,458, filed on Feb. 6, 2017.

(51) Int. Cl.
  *A61K 31/201* (2006.01)
  *A61P 3/04* (2006.01)

(52) U.S. Cl.
  CPC .............. *A61K 31/201* (2013.01); *A61P 3/04* (2018.01)

(58) Field of Classification Search
  None
  See application file for complete search history.

(56) References Cited

U.S. PATENT DOCUMENTS

| 2015/0051204 A1 | 2/2015 | Agreda Navajas et al. |
| 2016/0235789 A1 | 8/2016 | Wang |

OTHER PUBLICATIONS

Cypess et al., "Cold but not sympathomimetics activates human brown adipose tissue in vivo", Proc. Natl. Acad Sci., 2012, 109:10001-10005.
Frömel et al., "Soluble epoxide hydrolase regulates hematopoietic progenitor cell function via generation of fatty acid diols". Proc. Natl. Acad. Sci., 2012,109(25):9995-10000.
Guerra et al., "Emergence of Brown Adipocytes in White Fat in Mice Is Under Genetic Control" J. Clin. Invest., 1998, 102:412-420.
Hanssen et al., "Short-term cold acclimation improves insulin sensitivity in patients with type 2 diabetes mellitus", Nat. Med., 2015, 21:863-865.
Lee et al., "In vivo activity of epoxide hydrolase according to sequence variation affects the progression of human IgA nephropathy". Am. J. Physiol. Renal Physiol., 2011, 300: F1283-F1290.
Lynes et al., "Unwiring the transcriptional heat circuit", Proc. Natl. Acad. Sci., 2014, 111:14318-14319.
Nedergaard et al., "New Powers of Brown Fat: Fighting the Metabolic Syndrome", Cell. Metab., 2011, 13:238-240.
Oh et al., "GPR120 Is an Omega-3 Fatty Acid Receptor Mediating Potent Anti-inflammatory and Insulin-Sensitizing Effects", Cell, 2010, 142:687-698.
Petrovic et al., "Chronic Peroxisome Proliferator-activated Receptor y (PPAR y) Activation of Epididymally Derived White Adipocyte Cultures Reveals a Population of Thermogenically Competent, UCP1-containing Adipocytes Molecularly Distinct from Classic Brown Adipocytes", J. Biol. Chem., 2010, 285:7153-7164.
Romu et al., "A randomized trial of cold-exposure on energy expenditure and supraclavicular brawn adipose tissue volume in humans", Metabolism, 2016, 65:926-934.
Schuchardt et al., "Comparison of free serum oxylipin concentrations in hyper—vs. normolipidemic men", Prostaglandins Leukot Essent Fatty Acids, 2013, 89(1): 19-29.
Wang et al., "Brown Adipose Tissue in Humans Is Activated by Elevated Plasma Catecholamines Levels and Is Inversely Related to Central Obesity", PLoS ONE, 2011, 6(6): e21006. doi:10.1371/joumal.pone.0021006.
Wang et al., "Brown Adipose Tissue Activation Is Inversely Related to Central Obesity and Metabolic Parameters in Adult Human", PLoS ONE, 2015, 10(4):e0123795. doi:10.1371/journal.pone.0123795.
WO2018142379 International Search Report dated Jun. 26, 2018.
WO2018142379 IRPR dated Jun. 26, 2018.
Lynes et al., "The cold-induced lipokine 12,13-diHOME promotes fatty acid transport into brown adipose tissue", Nat Med., 2017, 23(5): 631-637. doi:10.1038/nm.4297.

*Primary Examiner* — Savitha M Rao
*Assistant Examiner* — Gregg Polansky
(74) *Attorney, Agent, or Firm* — Womble Bond Dickinson (US) LLP; Cristin Howley Cowles

(57) ABSTRACT

The invention includes methods and compositions for treating a metabolic disorder, such as metabolic syndrome, hyperlipidemia and associated disorders, such as obesity and diabetes. The invention includes a method of treating a human subject comprising administering 12,13-dihydroxy-9Z-octadecenoic acid (12,13-diHOME) to the subject. Further provided is the use of 12,13-diHOME as a biomarker for identifying brown adipose tissue (BAT) activation in human subjects.

8 Claims, 30 Drawing Sheets

Specification includes a Sequence Listing.

| Subject | 341-01 | 341-02 | 341-03 | 341-04 | 341-05 | 341-06 | 341-07 | 341-08 | 341-09 |
|---|---|---|---|---|---|---|---|---|---|
| Treatment | Cold | Cold | Cold | Cold | Cold | Cold | Cold | Cold | Cold |
| Code | 341-01-C | 341-02-C | 341-03-C | 341-04-C | 341-05-C | 341-06-C | 341-07-C | 341-08-C | 341-09-C |
| Species | | | | | | | | | |
| 15-d4-9-HODE | 0.0 | 0.0 | 0.0 | 0.0 | 0.0 | 0.0 | 0.0 | 0.0 | 0.0 |
| 9-oxoODE | 0.88207520 | 0.13772466 | 0.30110357 | 0.40821832 | 0.46119151 | 0.38578526 | 0.53432263 | 0.11439154 | 1.66230684 |
| 13-oxoODE | 0.84687575 | 0.23180595 | 0.08310963 | 0.37735672 | 0.44132719 | 0.37386546 | 0.38222553 | 0.13517607 | 1.23434785 |
| 9-HOTrE | 0.16697993 | 0.03389002 | 0.09420009 | 0.10592864 | 0.03706850 | 0.03113476 | 0.10456824 | 0.09061817 | 0.09564619 |
| 13-HOTrE/13-HOTrE(r) | 0.00000000 | 0.00212058 | 0.08444003 | 0.05244116 | 0.03325706 | 0.02133659 | 0.08367766 | 0.08187226 | 0.01455282 |
| 9-HODE | 3.91943541 | 1.22345046 | 0.67334838 | 1.31061089 | 1.85791051 | 1.01028230 | 1.96652953 | 0.94789945 | 5.64421903 |
| 13-HODE | 5.12097498 | 1.12833588 | 0.82559584 | 1.75618796 | 2.63683682 | 1.34057854 | 2.45533991 | 1.16158199 | 8.28243273 |
| 9(10)-EpOME | 2.20215408 | 0.74125195 | 0.31476495 | 0.27484368 | 0.53126437 | 0.37912148 | 0.71423327 | 0.49946771 | 1.97850056 |
| 12(13)-EpOME | 1.87320275 | 0.79379427 | 0.41317053 | 0.43629240 | 0.57413432 | 0.47966661 | 0.80479263 | 0.54021352 | 2.49837296 |
| 9,10-diHOME | 3.32725340 | 0.90768129 | 0.99019041 | 0.57254189 | 0.87079847 | 0.56103895 | 0.98862293 | 1.19871882 | 1.18568809 |
| 12,13-diHOME | 1.46875726 | 0.71652283 | 0.73638901 | 0.77912647 | 0.72679580 | 0.44177781 | 0.87099188 | 1.03721686 | 0.84714557 |
| 18-HEPE | 0.03482791 | 0.02260620 | 0.01393433 | 0.00128854 | 0.00452034 | 0.04189755 | 0.01187777 | 0.00000000 | 0.01691096 |
| 15-HEPE | 0.03995867 | 0.00000000 | 0.02781801 | 0.00839931 | 0.00649814 | 0.01278576 | 0.02861311 | 0.03783117 | 0.01252254 |
| 12-HEPE | 0.03797506 | 0.00000000 | 0.00669321 | 0.00331692 | 0.00000000 | 0.00000000 | 0.00649222 | 0.00000000 | 0.00596290 |
| 5-HEPE | 0.01443379 | 0.00895810 | 0.00591013 | 0.00831136 | 0.00000000 | 0.03951262 | 0.03103896 | 0.00000000 | 0.00000000 |
| 11-HEPE | 0.02245306 | 0.00000000 | 0.00000000 | 0.00310293 | 0.00000000 | 0.01149639 | 0.00475933 | 0.00000000 | 0.00391270 |
| 8-HEPE | 0.01577257 | 0.02781498 | 0.00000000 | 0.00000000 | 0.00814537 | 0.02094913 | 0.00000000 | 0.01078564 | 0.00000000 |
| 15-oxoETE | 0.01796359 | 0.00426954 | 0.00000000 | 0.00675241 | 0.00000000 | 0.01537980 | 0.00570874 | 0.03426826 | 0.00000000 |
| 9-HEPE | 0.00000000 | 0.00000000 | 0.00000000 | 0.00000000 | 0.00000000 | 0.00000000 | 0.00000000 | 0.00000000 | 0.00426522 |
| 14(15)-EET | 0.02118569 | 0.05183913 | 0.00000000 | 0.03391802? | 0.00000000 | 0.00947707 | 0.02463600 | 0.03407762 | 0.04587191 |
| 11(12)-EET | 0.01578896 | 0.03461700 | 0.04466404 | 0.00000000 | 0.02181022 | 0.00000000 | 0.00640353 | 0.05752618 | 0.05576792 |
| 8(9)-EET | 0.00000000 | 0.05018695 | 0.00929148 | 0.01584103 | 0.00000000 | 0.04858976 | 0.02459868 | 0.00464922 | 0.00000000 |
| 5(6)-EET | 0.00643152 | 0.00161645 | 0.00000000 | 0.00000000 | 0.00800458 | 0.01278646 | 0.03103985 | 0.03556599 | 0.02296320 |
| 15-HETE | 0.07191695 | 0.04967329 | 0.05489717 | 0.02416215 | 0.01823320 | 0.03551278 | 0.06858253 | 0.13475127 | 0.04767125 |
| 12-HETE | 0.16657980 | 0.08207757 | 0.04170098 | 0.03502839 | 0.04040702 | 0.14849331 | 0.27205378 | 0.11740046 | 0.04314802 |
| 5-HETE | 0.14201379 | 0.15667264 | 0.11004592 | 0.04914660 | 0.02794356 | 0.20771158 | 0.24605791 | 0.23871839 | 0.20932031 |
| 20-HETE | 0.05374696 | 0.13715509 | 0.02223985 | 0.01021937 | 0.00608212 | 0.01917904 | 0.01598346 | 0.00464922 | 0.08172544 |
| 11-HETE | 0.15478346 | 0.11454226 | 0.01821948 | 0.04501689 | 0.02968725 | 0.10309355 | 0.06475798 | 0.16665149 | 0.15898088 |
| 16-HETE | 0.04581254 | 0.00849749 | 0.03461581 | 0.01900474 | 0.02185598 | 0.02185598 | 0.01627169 | 0.01175279 | 0.01775930 |
| 17-HETE | 0.00000000 | 0.11589514 | 0.08511470 | 0.01190338 | 0.02470268 | 0.04160210 | 0.00000000 | 0.07104636 | 0.00000000 |
| 18-HETE | 0.02976464 | 0.03681365 | 0.00921048 | 0.01917963 | 0.00000000 | 0.07672836 | 0.00000000 | 0.10356622 | 0.07710787 |
| 9-HETE | 0.00643083 | 0.04239607 | 0.00000000 | 0.00000000 | 0.00000000 | 0.00551110 | 0.00000000 | 0.00000000 | 0.00913759 |
| 8-HETE | 0.03369040 | 0.04170806 | 0.00000000 | 0.01531632 | 0.00899042 | 0.00850767 | 0.00991709 | 0.03182722 | 0.00539254 |
| all trans-LTB4 | 0.01327579 | 0.03598697 | 0.00000000 | 0.00000000 | 0.00501076 | 0.00775905 | 0.00000000 | 0.00218906 | 0.02369955 |
| LTB4 | 0.01327579 | 0.00520328 | 0.00000000 | 0.00000000 | 0.00501076 | 0.00775905 | 0.00000000 | 0.01285761 | 0.00000000 |

FIG. 11A

| Subject | 341-01 | 341-02 | 341-03 | 341-04 | 341-05 | 341-06 | 341-07 | 341-08 | 341-09 |
|---|---|---|---|---|---|---|---|---|---|
| Treatment | Saline | Saline | Saline | Saline | Saline | Saline | Saline | Saline | Saline |
| Code | 341-01-S | 341-02-S | 341-03-S | 341-04-S | 341-05-S | 341-06-S | 341-07-S | 341-08-S | 341-09-S |
| Species | | | | | | | | | |
| 15-d4-9-HODE | 0.0 | 0.0 | 0.0 | 0.0 | 0.0 | 0.0 | 0.0 | 0.0 | 0.0 |
| 9-oxoODE | 0.22070346 | 0.13464997 | 0.67824337 | 0.33963432 | 0.12871609 | 0.16220992 | 0.06446726 | 0.36655777 | 0.62217710 |
| 13-oxoODE | 0.14931878 | 0.16398264 | 0.44110481 | 0.29814292 | 0.11087036 | 0.14897919 | 0.03521053 | 0.18031766 | 0.47868483 |
| 9-HOTrE | 0.05040424 | 0.03213139 | 0.03560319 | 0.05618638 | 0.02319030 | 0.01039693 | 0.02553466 | 0.04993029 | 0.05673979 |
| 13-HOTrE/13-HOTrE(r) | 0.07389398 | 0.03267962 | 0.31226557 | 0.09382568 | 0.00671887 | 0.01854387 | 0.03556270 | 0.04223872 | 0.12527225 |
| 9-HODE | 1.59699636 | 0.42535328 | 3.18619718 | 1.30629673 | 0.52118429 | 0.54076628 | 0.56493647 | 0.95049219 | 4.60993797 |
| 13-HODE | 1.62602974 | 0.47028437 | 3.37096622 | 2.23948275 | 0.54787381 | 0.62625744 | 0.67280668 | 1.20385351 | 2.73115580 |
| 9(10)-EpOME | 0.40949975 | 0.28451051 | 1.80132934 | 0.83020776 | 0.21822925 | 0.12019162 | 0.05716339 | 0.50686715 | 0.24733913 |
| 12(13)-EpOME | 0.48736350 | 0.46133654 | 1.67584874 | 0.91390139 | 0.25161919 | 0.24222062 | 0.08650000 | 0.60470406 | 1.58567437 |
| 9,10-dHOME | 0.49795281 | 1.16230900 | 0.52972917 | 0.80815770 | 0.41988789 | 0.24995267 | 0.35718634 | 1.20495860 | 0.77173535 |
| 12,13-dHOME | 0.45750170 | 0.53594509 | 0.36370236 | 0.67222662 | 0.29307866 | 0.19869644 | 0.23709399 | 0.48616595 | 0.68381850 |
| 18-HEPE | 0.00000000 | 0.01633175 | 0.03412209 | 0.04322722 | 0.00749832 | 0.00000000 | 0.00000000 | 0.00000000 | 0.00599058 |
| 15-HEPE | 0.00648206 | 0.07542249 | 0.00512205 | 0.03360370 | 0.00278939 | 0.04873730 | 0.03779358 | 0.01255589 | 0.01465769 |
| 12-HEPE | 0.01480579 | 0.00000000 | 0.00000000 | 0.02927001 | 0.00000000 | 0.01122213 | 0.03477062 | 0.00000000 | 0.00410264 |
| 5-HEPE | 0.02850702 | 0.02693501 | 0.01779496 | 0.00432579 | 0.00000000 | 0.00423175 | 0.02931917 | 0.00846928 | 0.00033205 |
| 11-HEPE | 0.00000000 | 0.01437334 | 0.00000000 | 0.01895096 | 0.00000000 | 0.00000000 | 0.00000000 | 0.01279124 | 0.00417701 |
| 8-HEPE | 0.00000000 | 0.00000000 | 0.00000000 | 0.00865140 | 0.00548504 | 0.03862309 | 0.02288272 | 0.00846970 | 0.00000000 |
| 15-oxoETE | 0.00000000 | 0.04323442 | 0.00000000 | 0.00000000 | 0.00548504 | 0.00458438 | 0.00000000 | 0.00000000 | 0.00389820 |
| 9-HEPE | 0.00000000 | 0.00000000 | 0.00000000 | 0.00000000 | 0.00354795 | 0.00000000 | 0.00000000 | 0.00000000 | 0.00000000 |
| 14(15)-EET | 0.00048871 | 0.00000000 | 0.00000000 | 0.00432557 | 0.00000000 | 0.01722085 | 0.00000000 | 0.00919167 | 0.00000000 |
| 11(12)-EET | 0.01881642 | 0.04062346 | 0.00531622 | 0.00168112 | 0.00278909 | 0.02441701 | 0.02822197 | 0.00000000 | 0.00961029 |
| 8(9)-EET | 0.03453190 | 0.10462385 | 0.02023739 | 0.00000000 | 0.00957971 | 0.03720013 | 0.00530879 | 0.01693959 | 0.00449927 |
| 5(6)-EET | 0.01482362 | 0.05393147 | 0.01920405 | 0.00432579 | 0.00154816 | 0.00000000 | 0.00000000 | 0.03802619 | 0.00381695 |
| 15-HETE | 0.08072385 | 0.11617988 | 0.01358925 | 0.04751897 | 0.02529085 | 0.02811637 | 0.03147345 | 0.01461535 | 0.03564841 |
| 12-HETE | 0.04076668 | 0.24696941 | 0.02658043 | 0.08995519 | 0.02911897 | 0.02483710 | 0.92245723 | 0.00872025 | 0.05640258 |
| 5-HETE | 0.19722658 | 0.31201862 | 0.08347809 | 0.04301536 | 0.02577249 | 0.05942672 | 0.08752551 | 0.12765647 | 0.09497188 |
| 20-HETE | 0.06587482 | 0.07824381 | 0.00000000 | 0.00000000 | 0.00294681 | 0.02222963 | 0.00535926 | 0.00788525 | 0.01374217 |
| 11-HETE | 0.11062228 | 0.09429788 | 0.01316201 | 0.29811177 | 0.07710361 | 0.07707103 | 0.70649298 | 0.08582017 | 0.04986108 |
| 16-HETE | 0.01206397 | 0.02780117 | 0.00960223 | 0.00397036 | 0.00000000 | 0.03448142 | 0.00000000 | 0.01086333 | 0.00711744 |
| 17-HETE | 0.04626907 | 0.10026577 | 0.06238874 | 0.12378804 | 0.02452737 | 0.04716966 | 0.01727634 | 0.24170241 | 0.02713897 |
| 18-HETE | 0.07537659 | 0.19277452 | 0.03436163 | 0.03017551 | 0.04201908 | 0.05321102 | 0.00000000 | 0.00000000 | 0.01730326 |
| 9-HETE | 0.03682737 | 0.02874102 | 0.00531599 | 0.00432558 | 0.00393721 | 0.00000000 | 0.03985595 | 0.00768525 | 0.01199032 |
| 8-HETE | 0.00000000 | 0.05428681 | 0.01801625 | 0.29821177 | 0.07710361 | 0.00000000 | 0.06338788 | 0.03307261 | 0.01220137 |
| all trans-LTB4 | 0.01036466 | 0.00000000 | 0.00960223 | 0.00873930 | 0.00843015 | 0.00000000 | 0.00000000 | 0.01086333 | 0.00000000 |
| LTB4 | 0.00000000 | 0.00000000 | 0.00249753 | 0.00708181 | 0.00000000 | 0.00000000 | 0.00000000 | 0.00385560 | 0.00000000 |

FIG. 11B

| Subject | 341-01 | 341-02 | 341-03 | 341-04 | 341-05 | 341-06 | 341-07 | 341-08 | 341-09 |
|---|---|---|---|---|---|---|---|---|---|
| Treatment | Cold | Cold | Cold | Cold | Cold | Cold | Cold | Cold | Cold |
| 5,6-diHETE | 0.04434704 | 0.03750288 | 0.01147270 | 0.00961816 | 0.00000000 | 0.03576784 | 0.00000000 | 0.00000000 | 0.00781009 |
| 5,15-diHETE | 0.00000000 | 0.00000000 | 0.00000000 | 0.00000000 | 0.00000000 | 0.00000000 | 0.00000000 | 0.00000000 | 0.00492520 |
| Hepoxilin A3 | 0.01265234 | 0.00000000 | 0.01071905 | 0.00000000 | 0.00000000 | 0.00000000 | 0.00000000 | 0.00000000 | 0.00000000 |
| 17-HDHA | 0.13086115 | 0.03094994 | 0.00000000 | 0.00000000 | 0.00000000 | 0.00000000 | 0.06339340 | 0.14383265 | 0.00000000 |
| 14-HDHA | 0.01104692 | 0.03963729 | 0.00923092 | 0.00331692 | 0.00223335 | 0.02095718 | 0.00401189 | 0.04854841 | 0.00596288 |
| 7-HDHA | 0.00000000 | 0.00520821 | 0.00000000 | 0.00371737 | 0.00000000 | 0.03399313 | 0.02354642 | 0.00000000 | 0.00000000 |
| 4-HDHA | 0.02220410 | 0.00000000 | 0.00925261 | 0.00780255 | 0.00606823 | 0.02094808 | 0.02561428 | 0.00000000 | 0.01192581 |
| 8-HDHA | 0.01626243 | 0.00000000 | 0.00000000 | 0.00000000 | 0.00000000 | 0.02094824 | 0.03876309 | 0.00000000 | 0.02739624 |
| 10-HDHA | 0.01577190 | 0.02205848 | 0.03543268 | 0.00000000 | 0.00904059 | 0.00000000 | 0.00000000 | 0.03117691 | 0.00000000 |
| 11-HDHA | 0.00000000 | 0.00000000 | 0.01846295 | 0.00000000 | 0.00608207 | 0.00000000 | 0.00000000 | 0.00881858 | 0.00596318 |
| 13-HDHA | 0.02699201 | 0.00000000 | 0.09923194 | 0.00331681 | 0.00452035 | 0.00787255 | 0.01280712 | 0.04021322 | 0.00000000 |
| 16-HDHA | 0.00000000 | 0.01402686 | 0.00923179 | 0.00521808 | 0.03154359 | 0.03154359 | 0.00946175 | 0.03556135 | 0.00000000 |
| 20-HDHA | 0.00000000 | 0.00519654 | 0.03543118 | 0.01199923 | 0.00000000 | 0.00000000 | 0.00476209 | 0.01793754 | 0.02291030 |
| 19(20)-EpDPE | 0.00000000 | 0.00519984 | 0.00477116 | 0.00000000 | 0.00000000 | 0.00000000 | 0.00000000 | 0.01286167 | 0.00000000 |
| 16(17)-EpDPE | 0.00000000 | 0.00169609 | 0.00000000 | 0.00000000 | 0.00263481 | 0.01545260 | 0.00000000 | 0.04020443 | 0.00000000 |
| PGE2/PGD2 | 0.03237649 | 0.03311641 | 0.00162726 | 0.00310629 | 0.00000000 | 0.00786371 | 0.00534238 | 0.01956326 | 0.00613352 |
| PGD2 | 0.05110797 | 0.00000000 | 0.00299722 | 0.00000000 | 0.00000000 | 0.00000000 | 0.00000000 | 0.00539098 | 0.00955062 |
| LXA4 | 0.03969985 | 0.01253619 | 0.00335969 | 0.00000000 | 0.00517021 | 0.00518695 | 0.01116179 | 0.00000000 | 0.00332980 |
| LXB4 | 0.02114888 | 0.00283358 | 0.00318569 | 0.00604490 | 0.00000000 | 0.00000000 | 0.00000000 | 0.00000000 | 0.00194575 |
| 15-keto-PGF2a | 0.00000000 | 0.00000000 | 0.00368083 | 0.00000000 | 0.00000000 | 0.00353299 | 0.01212309 | 0.00000000 | 0.01668138 |
| 13,14-dihydro-15-keto PGE2 | 0.00476807 | 0.01285741 | 0.00000000 | 0.00697658 | 0.00000000 | 0.00000000 | 0.00825804 | 0.00278101 | 0.00666099 |
| 13,14-dihydro-15-keto PGD2 | 0.04834704 | 0.00998238 | 0.00162723 | 0.00546839 | 0.00189556 | 0.00537476 | 0.01599245 | 0.00789616 | 0.00666484 |
| PGF2a | 0.03029478 | 0.00848361 | 0.03218534 | 0.00894722 | 0.00526992 | 0.00342366 | 0.02811518 | 0.00521461 | 0.01039009 |
| PGE1/D1 | 0.00477080 | 0.02794274 | 0.00000000 | 0.00681215 | 0.00000000 | 0.00518683 | 0.01599794 | 0.00821993 | 0.02295678 |
| 8-iso PGF2a | 0.03297230 | 0.00848361 | 0.03318834 | 0.00894392 | 0.00526964 | 0.00247984 | 0.02182173 | 0.00432122 | 0.00780757 |
| 5-iPF2a-VI | 0.01220498 | 0.01362698 | 0.00184412 | 0.00970778 | 0.00000000 | 0.00353314 | 0.01108631 | 0.00000000 | 0.01640537 |
| Maresin1 | 0.00000000 | 0.00000000 | 0.00000000 | 0.00000000 | 0.00000000 | 0.00000000 | 0.00000000 | 0.00000000 | 0.00000000 |
| PD1 | 0.00000000 | 0.00258433 | 0.00318108 | 0.00310627 | 0.00294010 | 0.00000000 | 0.00000000 | 0.00666235 | 0.00000000 |
| TxB2 | 0.15578249 | 0.01980041 | 0.01436194 | 0.00537447 | 0.04811491 | 0.00586518 | 0.17335966 | 0.00958853 | 0.05629110 |
| 6-keto-PGF1a | 0.00000000 | 0.00848333 | 0.00000000 | 0.00294026 | 0.00294026 | 0.00000000 | 0.00316439 | 0.01108041 | 0.00000000 |
| 19/20-OH PGF2a | 0.00000000 | 0.00000000 | 0.00162726 | 0.00402614 | 0.00000000 | 0.00600204 | 0.00316430 | 0.00000000 | 0.00000000 |
| RvD1 | 0.00000000 | 0.00000000 | 0.00000000 | 0.00000000 | 0.00263174 | 0.00000000 | 0.00311709 | 0.00207440 | 0.00286939 |
| RvD2 | 0.00000000 | 0.00000000 | 0.00000000 | 0.00681215 | 0.00000000 | 0.00000000 | 0.00693990 | 0.00207584 | 0.00000000 |
| LTE4 | 0.00000000 | 0.00000000 | 0.00000000 | 0.00000000 | 0.00000000 | 0.00000000 | 0.00000000 | 0.00000000 | 0.00000000 |
| LTD4 | 0.00603215 | 0.00000000 | 0.00000000 | 0.00000000 | 0.00209026 | 0.00000000 | 0.00000000 | 0.00000000 | 0.00000000 |
| LTC4 | 0.00000000 | 0.00374594 | 0.00000000 | 0.00310614 | 0.00000000 | 0.00000000 | 0.00251544 | 0.00000000 | 0.00000000 |

FIG. 11C

| Subject Treatment | 341-01 Saline | 341-02 Saline | 341-03 Saline | 341-04 Saline | 341-05 Saline | 341-06 Saline | 341-07 Saline | 341-08 Saline | 341-09 Saline |
|---|---|---|---|---|---|---|---|---|---|
| 5,6-diHETE | 0.01258684 | 0.00000000 | 0.00082286 | 0.00000000 | 0.00000000 | 0.00878693 | 0.00395142 | 0.00000000 | 0.00109043 |
| 5,15-diHETE | 0.00000000 | 0.00752271 | 0.00000000 | 0.00000000 | 0.00000000 | 0.00570484 | 0.00000000 | 0.00000000 | 0.00000000 |
| Hepoxilin A3 | 0.00000000 | 0.01362103 | 0.00000000 | 0.00000000 | 0.00000000 | 0.00000000 | 0.00452613 | 0.00386563 | 0.00766148 |
| 17-HDHA | 0.00000000 | 0.00000000 | 0.02119478 | 0.00000000 | 0.08715058 | 0.00000000 | 0.00000000 | 0.01418545 | 0.00834500 |
| 14-HDHA | 0.03129745 | 0.03253428 | 0.00000000 | 0.00000000 | 0.00787485 | 0.00000000 | 0.12173980 | 0.00000000 | 0.00435603 |
| 7-HDHA | 0.00000000 | 0.00000000 | 0.00512305 | 0.00432564 | 0.00000000 | 0.00000000 | 0.00000000 | 0.00000000 | 0.00435581 |
| 4-HDHA | 0.00000000 | 0.02693615 | 0.00000000 | 0.02319510 | 0.00546205 | 0.02171119 | 0.02822318 | 0.01547035 | 0.00416748 |
| 8-HDHA | 0.00000000 | 0.00000000 | 0.00450554 | 0.01895612 | 0.00000000 | 0.00000000 | 0.00000000 | 0.00000000 | 0.00416525 |
| 10-HDHA | 0.00000000 | 0.01484626 | 0.01491797 | 0.00432579 | 0.00812764 | 0.01425676 | 0.00531269 | 0.00000000 | 0.00000000 |
| 11-HDHA | 0.00000000 | 0.05170875 | 0.00000000 | 0.00000000 | 0.00278911 | 0.00000000 | 0.02888005 | 0.00000000 | 0.00434652 |
| 13-HDHA | 0.00000000 | 0.04690383 | 0.00000000 | 0.06286332 | 0.00920093 | 0.00000000 | 0.08846250 | 0.03119730 | 0.00000000 |
| 16-HDHA | 0.00000000 | 0.05051611 | 0.00669153 | 0.00222847 | 0.00932429 | 0.00860048 | 0.07601718 | 0.00846921 | 0.00600437 |
| 20-HDHA | 0.06892118 | 0.05129034 | 0.00888749 | 0.00000000 | 0.01044571 | 0.00000000 | 0.02444360 | 0.01040728 | 0.01345364 |
| 19(20)-EpDPE | 0.05750689 | 0.00000000 | 0.00000000 | 0.00934214 | 0.00934214 | 0.00000000 | 0.02291146 | 0.00000000 | 0.00000000 |
| 16(17)-EpDPE | 0.01480579 | 0.00000000 | 0.02451986 | 0.00419905 | 0.00492333 | 0.00000000 | 0.02291011 | 0.01471839 | 0.00000000 |
| PGE2/PGD2 | 0.00180509 | 0.00403581 | 0.00601951 | 0.00436398 | 0.02118443 | 0.00148337 | 0.04024763 | 0.00934356 | 0.00283751 |
| PGD2 | 0.00000000 | 0.00382797 | 0.00208890 | 0.00276077 | 0.00000000 | 0.00328019 | 0.02318241 | 0.00000000 | 0.00325890 |
| LXA4 | 0.00564954 | 0.00000000 | 0.00862614 | 0.00766044 | 0.00323691 | 0.00000000 | 0.00000000 | 0.00000000 | 0.00104566 |
| LXB4 | 0.01881837 | 0.02066103 | 0.00000000 | 0.00000000 | 0.02355869 | 0.00000000 | 0.01220011 | 0.00000000 | 0.00120800 |
| 15-keto-PGF2a | 0.01801200 | 0.00287760 | 0.00166592 | 0.00000000 | 0.00866126 | 0.00045731 | 0.00204585 | 0.00313710 | 0.00216842 |
| 13,14-dihydro-15-keto PGE2 | 0.00853768 | 0.00553044 | 0.00000000 | 0.00455911 | 0.00308360 | 0.00000000 | 0.02082041 | 0.00000000 | 0.00262427 |
| 13,14-dihydro-15-keto PGD2 | 0.01078050 | 0.01515891 | 0.00000000 | 0.00227298 | 0.00000000 | 0.00244245 | 0.01225892 | 0.00175041 | 0.00000000 |
| PGF2a | 0.00000000 | 0.00562970 | 0.00713767 | 0.00867168 | 0.00962842 | 0.00000000 | 0.01013146 | 0.00171746 | 0.00444059 |
| PGE1/D1 | 0.00281416 | 0.02229943 | 0.00000000 | 0.00658218 | 0.00961785 | 0.00618589 | 0.03967214 | 0.00548662 | 0.00763858 |
| 8-iso PGF2a | 0.00000000 | 0.00562970 | 0.00601947 | 0.00746147 | 0.00769415 | 0.00000000 | 0.00362795 | 0.00174637 | 0.00652314 |
| 5-iPF2a-VI | 0.00000000 | 0.01698265 | 0.00206176 | 0.00435662 | 0.00000000 | 0.00444197 | 0.00000000 | 0.00175036 | 0.00000000 |
| Maresin1 | 0.00000000 | 0.00000000 | 0.00000000 | 0.00000000 | 0.00000000 | 0.00000000 | 0.00000000 | 0.00000000 | 0.00000000 |
| PD1 | 0.00000000 | 0.00562975 | 0.00000000 | 0.00136330 | 0.00962882 | 0.00407104 | 0.00656500 | 0.00000000 | 0.00241397 |
| TxB2 | 0.00000000 | 0.01535797 | 0.00000000 | 0.02116264 | 0.10979916 | 0.00296675 | 0.42155733 | 0.02836876 | 0.00853881 |
| 6-keto-PGF1a | 0.00000000 | 0.00000000 | 0.00601946 | 0.00000000 | 0.00327660 | 0.00000000 | 0.01927389 | 0.00524866 | 0.00114938 |
| 19/20-OH PGF2a | 0.00281505 | 0.00000000 | 0.00206177 | 0.00000000 | 0.00000000 | 0.00000000 | 0.00000000 | 0.00000000 | 0.00340826 |
| RvD1 | 0.00000000 | 0.00000000 | 0.00000000 | 0.00000000 | 0.00814485 | 0.00000000 | 0.00000000 | 0.00175041 | 0.00000000 |
| RvD2 | 0.00274752 | 0.00675513 | 0.00000000 | 0.00000000 | 0.00327660 | 0.00000000 | 0.00000000 | 0.00000000 | 0.00761101 |
| LTE4 | 0.00000000 | 0.00000000 | 0.00000000 | 0.00000000 | 0.00000000 | 0.00144572 | 0.00000000 | 0.00000000 | 0.00000000 |
| LTD4 | 0.00000000 | 0.00000000 | 0.00000000 | 0.00000000 | 0.00000000 | 0.00000000 | 0.00319376 | 0.00000000 | 0.00000000 |
| LTC4 | 0.00000000 | 0.00000000 | 0.00000000 | 0.00000000 | 0.00000000 | 0.00148337 | 0.00000000 | 0.00206371 | 0.00000000 |

FIG. 11D

| Subject | 341-01 | 341-02 | 341-03 | 341-04 | 341-05 | 341-06 | 341-07 | 341-08 | 341-09 |
|---|---|---|---|---|---|---|---|---|---|
| Treatment | Cold | Cold | Cold | Cold | Cold | Cold | Cold | Cold | Cold |
| PGF1a | 0.00000000 | 0.00282650 | 0.05960986 | 0.00379564 | 0.00000000 | 0.00000000 | 0.00000000 | 0.00000000 | 0.00000000 |
| 15-keto-PGE2 | 0.00603215 | 0.00000000 | 0.00000000 | 0.00000000 | 0.00000000 | 0.00518699 | 0.00000000 | 0.00000000 | 0.00000000 |
| PGD3 | 0.00000000 | 0.01622295 | 0.00481326 | 0.00402611 | 0.00558118 | 0.00000000 | 0.00000000 | 0.00562756 | 0.00000000 |
| PGA2/PGJ2 | 0.01048766 | 0.01085063 | 0.00318108 | 0.00703436 | 0.00153868 | 0.00336492 | 0.00543520 | 0.00813370 | 0.00000000 |
| PGB2 | 0.00477386 | 0.00515664 | 0.00000000 | 0.01023857 | 0.00000000 | 0.00000000 | 0.00000000 | 0.00262997 | 0.00000000 |
| 15-deoxy-delta12,14-PGD2 | 0.00880852 | 0.00284002 | 0.00000000 | 0.00000000 | 0.01155394 | 0.01012046 | 0.01599827 | 0.00521788 | 0.00000000 |
| 5,6-DiHETrE | 0.00345260 | 0.00266656 | 0.01071895 | 0.01428401 | 0.06458497 | 0.00775866 | 0.04597991 | 0.00000000 | 0.01055590 |
| 8,9-DiHETrE | 0.01894492 | 0.02245293 | 0.00000000 | 0.00211861 | 0.00193267 | 0.00000000 | 0.00632079 | 0.01210574 | 0.01377357 |
| 11,12-DiHETrE | 0.13832154 | 0.01530025 | 0.02961696 | 0.03621561 | 0.06796210 | 0.14266708 | 0.18449487 | 0.03568834 | 0.13386157 |
| 14,15-DiHETrE | 0.25314244 | 0.28518020 | 0.08407026 | 0.06673701 | 0.08865614 | 0.20891383 | 0.14621531 | 0.08789911 | 0.17444377 |
| 5-HETrE | 0.00000000 | 0.02911327 | 0.02872587 | 0.00412028 | 0.00000000 | 0.02094915 | 0.00000000 | 0.00548410 | 0.03483118 |
| 8-HETrE | 0.07079045 | 0.07777401 | 0.04262773 | 0.00667031 | 0.00000000 | 0.05226377 | 0.00000000 | 0.00000000 | 0.13868969 |
| 15-HETrE | 0.12283663 | 0.13386140 | 0.03874481 | 0.07179680 | 0.07878727 | 0.14105611 | 0.04945661 | 0.41635866 | 0.32535658 |
| 19,20-DiHDPA | 0.19657519 | 0.01488160 | 0.09533832 | 0.01938806 | 0.09466181 | 0.15260692 | 0.12946520 | 0.05666532 | 0.10466447 |
| 2,3-dinor-11beta-PGF2a | 0.00000000 | 0.00000000 | 0.00162726 | 0.00000000 | 0.00000000 | 0.00000000 | 0.00000000 | 0.00000000 | 0.00000000 |
| 15-deoxy-delta12,14-PGJ2 | 0.00000000 | 0.03392007 | 0.01693021 | 0.00315956 | 0.01354647 | 0.03424425 | 0.02280314 | 0.00578632 | 0.01711792 |
| TxB3 | 0.00000000 | 0.00000000 | 0.00235668 | 0.00310616 | 0.00263493 | 0.00353314 | 0.00000000 | 0.00655911 | 0.00801773 |
| Tetranor-12-HETE | 0.01286271 | 0.02285245 | 0.00923179 | 0.03868014 | 0.02395912 | 0.07868379 | 0.06323881 | 0.02416028 | 0.02974028 |
| Precursors | | | | | | | | | |
| Docosanoids | 0.44457102 | 0.15078243 | 0.24057397 | 0.06849294 | 0.12523814 | 0.29840486 | 0.32919493 | 0.39769005 | 0.19809762 |
| Eicosanoids | 3.16430801 | 2.06535800 | 1.35995176 | 1.21503573 | 1.24483445 | 1.69986643 | 2.34518460 | 2.42629028 | 2.37806793 |
| Octadecanoids | 9.30854111 | 2.84614814 | 2.19653918 | 2.17518185 | 2.91578437 | 2.21061251 | 3.52876524 | 2.51858581 | 8.65586249 |
| Inflammatory | | | | | | | | | |
| Anti-inflammatory | 7.77025571 | 3.04211120 | 2.15121665 | 2.91924816 | 3.49962083 | 2.87531290 | 4.31060166 | 3.40145576 | 8.89323730 |
| Pro-inflammatory | 13.92532857 | 4.20927298 | 3.12483579 | 3.62302841 | 5.20165711 | 3.60107252 | 6.17272985 | 4.04290409 | 16.02584389 |
| Enzymatic COX | 0.39802421 | 0.14483448 | 0.10184432 | 0.06980047 | 0.07050444 | 0.05878489 | 0.27404050 | 0.11924542 | 0.13405346 |
| CYP450 | 14.25031086 | 4.34536852 | 3.26474616 | 3.66621017 | 5.38277009 | 3.97172755 | 6.26394498 | 4.06039291 | 16.36641673 |
| LOX | 3.24506460 | 2.92829671 | 2.30022923 | 3.25252239 | 3.81652389 | 2.91246982 | 4.69918886 | 3.41448326 | 10.27976022 |

FIG. 11E

| Subject | 341-01 | 341-02 | 341-03 | 341-04 | 341-05 | 341-06 | 341-07 | 341-08 | 341-09 |
|---|---|---|---|---|---|---|---|---|---|
| Treatment | Saline | Saline | Saline | Saline | Saline | Saline | Saline | Saline | Saline |
| PGF1a | 0.00000000 | 0.07473816 | 0.00860168 | 0.05117547 | 0.00000000 | 0.00000000 | 0.00000000 | 0.00000000 | 0.06129607 |
| 15-keto-PGE2 | 0.00000000 | 0.00000000 | 0.00000000 | 0.00000000 | 0.00000000 | 0.00000000 | 0.00000000 | 0.00000000 | 0.00000000 |
| PGD3 | 0.00000000 | 0.00470715 | 0.00000000 | 0.00240464 | 0.00327344 | 0.00000000 | 0.02094648 | 0.00000000 | 0.00253709 |
| PGA2/PGJ2 | 0.00074161 | 0.01062494 | 0.00650242 | 0.00892767 | 0.00962882 | 0.00000000 | 0.00000000 | 0.00116949 | 0.00000000 |
| PGB2 | 0.00514772 | 0.00000000 | 0.00470749 | 0.00000000 | 0.00327646 | 0.00000000 | 0.00428663 | 0.00249190 | 0.00000000 |
| 15-deoxy-delta12,14-PGD2 | 0.00000000 | 0.00000000 | 0.00465665 | 0.00276347 | 0.01978713 | 0.00296673 | 0.02575126 | 0.00350073 | 0.00374253 |
| 5,6-DiHETrE | 0.03623538 | 0.02660184 | 0.00935528 | 0.00465124 | 0.00000000 | 0.02635985 | 0.00644169 | 0.00000000 | 0.00190449 |
| 8,9-DiHETrE | 0.02176487 | 0.02713225 | 0.02691133 | 0.00988760 | 0.03365783 | 0.01879593 | 0.00584746 | 0.02920653 | 0.00761833 |
| 11,12-DiHETrE | 0.16961684 | 0.11246387 | 0.04509038 | 0.02393381 | 0.02095105 | 0.17118215 | 0.01979974 | 0.05983042 | 0.01741919 |
| 14,15-DiHETrE | 0.18282615 | 0.17465069 | 0.15817538 | 0.04275780 | 0.20256671 | 0.22901717 | 0.04850597 | 0.10086025 | 0.07283636 |
| 5-HETrE | 0.11552983 | 0.00000000 | 0.00532609 | 0.00000000 | 0.00000000 | 0.00000000 | 0.00000000 | 0.04721793 | 0.01008503 |
| 8-HETrE | 0.02130126 | 0.02693501 | 0.00000000 | 0.03359437 | 0.00000000 | 0.03151187 | 0.07847393 | 0.00846921 | 0.00417684 |
| 15-HETrE | 0.32187915 | 0.91450788 | 0.05276736 | 0.33742994 | 0.04114536 | 0.06621080 | 0.36815073 | 0.26520039 | 0.02333572 |
| 19,20-DiHDPA | 0.210546674 | 0.16100974 | 0.03036406 | 0.04923989 | 0.17368477 | 0.18713177 | 0.06225690 | 0.06385036 | 0.10421156 |
| 2,3-dinor-11beta-PGF2a | 0.00000000 | 0.00000000 | 0.00000000 | 0.00000000 | 0.00000000 | 0.00000000 | 0.00000000 | 0.00000000 | 0.00000000 |
| 15-deoxy-delta12,14-PGJ2 | 0.01533068 | 0.04838009 | 0.01499458 | 0.00112402 | 0.02377063 | 0.01067354 | 0.00773433 | 0.00431489 | 0.00253698 |
| TxB3 | 0.00654388 | 0.00000000 | 0.00157938 | 0.00000000 | 0.00584882 | 0.00000000 | 0.04531966 | 0.00000000 | 0.00000000 |
| Tetranor-12-HETE | 0.09532808 | 0.05031429 | 0.02126462 | 0.09187375 | 0.02698304 | 0.00000000 | 0.04328249 | 0.00000000 | 0.02259983 |
| Precursors | | | | | | | | | |
| Docosanoids | 0.38108731 | 0.46634915 | 0.09580794 | 0.16949095 | 0.33154691 | 0.23614217 | 0.46277348 | 0.14919596 | 0.16447540 |
| Eicosanoids | 1.94569993 | 3.00003896 | 0.95737846 | 1.52644377 | 0.91967462 | 1.04405385 | 2.54916794 | 1.32541319 | 1.11153383 |
| Octadecanoids | 1.81524255 | 2.23872005 | 5.16185862 | 3.24623048 | 1.15851309 | 0.92995095 | 0.62606218 | 2.91333553 | 3.76237058 |
| Inflammatory | | | | | | | | | |
| Anti-inflammatory | 3.45884187 | 3.29394784 | 4.52289720 | 3.12171484 | 1.61600558 | 1.77581688 | 1.94358209 | 2.35996116 | 6.20284882 |
| Pro-inflammatory | 3.71776977 | 3.23782076 | 8.51788670 | 5.38231456 | 1.70707805 | 1.53655225 | 2.42593049 | 4.11130551 | 6.26715966 |
| Enzymatic COX | 0.08429828 | 0.18105493 | 0.07794880 | 0.12147372 | 0.20968652 | 0.01914308 | 0.55547977 | 0.06969611 | 0.09098157 |
| CYP450 | 4.14311064 | 3.46957095 | 8.41098624 | 5.30341928 | 2.01566371 | 2.13121500 | 1.51813757 | 4.27567713 | 6.27617438 |
| LOX | 3.30169720 | 3.06819946 | 5.27858119 | 3.55813921 | 1.36076381 | 1.37873527 | 2.82287832 | 2.59977874 | 6.80387067 |

FIG. 11F

METHODS AND COMPOSITIONS FOR TREATING METABOLIC DISORDERS

RELATED APPLICATIONS

This application is a Continuation of International Application No. PCT/IB2018/050744, filed on Feb. 6, 2018, which claims priority to U.S. Provisional Patent Application No. 62/455,458, filed on Feb. 6, 2017, and entitled "Methods and Compositions for Treating Metabolic Disorders." Each of the foregoing applications is incorporated herein by reference in its entirety.

GOVERNMENT INTEREST

This invention was made with Government support under grant number R01DK077097 awarded by the U.S. National Institutes of Health (NIH). The Government has certain rights in this invention.

SEQUENCE LISTING

The instant application contains a Sequence Listing which has been filed electronically in ASCII format and is hereby incorporated by reference in its entirety. Said ASCII copy, created on Aug. 28, 2019, is named J103021_1050US_PCT_SL.txt and is 3,623 bytes in size.

BACKGROUND OF THE INVENTION

In mammals, there are two functionally different types of fat: white adipose tissue (WAT), the primary site of triglyceride storage, and brown adipose tissue (BAT), which is specialized in thermogenic energy expenditure (Cannon B., et al., *Physiol. Rev.* 84:277-359, 2004). In addition to the classical brown adipocytes, which form a discrete depot and exert a high level of basal thermogenic capacity, UCP1-positive "beige" or "brite" adipocytes can be recruited within WAT upon chronic cold or β3-adrenergic stimulation (Guerra C., et al., *J. Clin. Invest.* 102:412-420, 1998; Petrovic N. et al., *J. Biol. Chem.* 285:7153-7164, 2010; Harms, M. & Seale, P. *Nat Med.* 19, 1252-1263, 2013; and Nedergaard J., et al., *Cell. Metab.* 13:238-240, 2011).

Owing to the immense capacity of BAT and beige adipose tissue to combust fuels for heat production in adult humans, increasing the amount or activity of brown/beige fat constitutes an appealing approach for treatment or prevention of metabolic disorders (Townsend, K. L. & Tseng, Y. H., *Adipocyte.* 1, 13-24 (2012); Lynes, M. D. & Tseng, Y. H., *Proc Natl Acad Sci. U.S.A.* 111, 14318-14319 (2014)). Cold exposure in humans can improve nutrient metabolism and enhance energy expenditure by activating BAT, pointing towards a therapeutic potential of BAT in humans (Romu, T., et al., *Metabolism.* 65, 926-934 (2016); Schellen, L., et al., *Physiol Behav.* 107, 252-261 (2012); Hanssen, M. J. et al., *Nat. Med.* 21, 863-865 (2015). These therapies, however, are time consuming and uncomfortable, increasing the need in the art for the development of therapies to treat metabolic disorders.

SUMMARY OF THE INVENTION

The present invention is based, at least in part, on the discovery that certain thermogenic lipokines can act as indicators and mediators of brown adipose tissue (BAT) activity in response to cold. A described herein, 12,13-dihydroxy-9Z-octadecenoic acid (12,13-diHOME) is produced in response to cold, acutely activates fuel uptake by BAT, and enhances cold tolerance, resulting in a decrease in the level of circulating triglycerides in the blood of a subject. Thus, the present invention includes methods and compositions for treating disorders and conditions that would benefit from BAT activation, such as metabolic disorders (e.g., metabolic syndrome, insulin resistance, hyperlipidemia and disorders associated with hyperlipidemia).

In one aspect, the present invention provides methods and compositions for treating a subject having a disorder characterized by high level of lipids (e.g., fats, cholesterol and triglycerides) in the blood, e.g., a metabolic disorder such as hyperlipidemia or a disorder associated with hyperlipidemia, by administering a composition comprising a thermogenic lipokine, e.g., 12,13-diHOME, to the subject. In another aspect, the present invention provides methods and compositions relating to decreasing the level of circulating triglycerides in the blood of a subject in need thereof by administering to the subject a thermogenic lipokine, e.g., 12,13-diHOME.

Accordingly, in one aspect, the invention provides a method of treating a human subject having a metabolic disorder, said method comprising administering an effective amount of 12,13-dihydroxy-9Z-octadecenoic acid (12,13-diHOME), a stereoisomer, a geometric isomer, or a pharmaceutically acceptable salt thereof, to a subject having a metabolic disorder.

In one embodiment of the foregoing aspects, the metabolic disorder is hyperlipidemia, insulin resistance, metabolic syndrome, obesity, and/or diabetes. In some embodiments, the human subject has hyperlipidemia and a disorder associated with hyperlipidemia which is obesity, diabetes, atherosclerosis, and/or heart disease.

In another aspect, the invention provides a method of treating a human subject having heart disease comprising administering an effective amount of 12,13-diHOME, a stereoisomer, a geometric isomer, or a pharmaceutically acceptable salt thereof, to a subject having heart disease.

In one embodiment of the foregoing aspects, the human subject further has hyperlipidemia.

In one embodiment of the foregoing aspects, the human subject has at least one of the following characteristics: a plasma alanine transaminase (ALAT) level greater than 0.6 μkat/l; a Body Mass Index (BMI) 30 or more; a Homeostatic Model Assessment of Insulin Resistance (HOMA-IR) score of 1.9 or more; a plasma triglyceride level greater than 1.7 mmol/l; a plasma aspartate transaminase (ASAT) level of greater than 0.3 μkat/l for a male subject or a plasma ASAT level of greater than 0.6 μkat/l for a female subject; a plasma leptin level of 40 ng/ml or more; or a plasma gGT level of 0.9 μkat/l or greater for a male subject or a plasma gGT level of 0.6 μkat/l or greater for a female subject.

In certain embodiments, the effective amount of 12,13-diHOME is an amount that decreases the level of circulating triglycerides in the blood of the human subject relative to a level of circulating triglycerides prior to treatment of the subject with 12,13-diHOME.

In one embodiment, the method of detecting a 12,13-diHOME level in a human subject comprises obtaining a plasma sample from the human subject and detecting 12,13-diHOME levels in the plasma sample by mass spectrometry.

In certain embodiments, the invention features a method of determining whether a human subject has brown adipose tissue (BAT) activation, said method comprising determining the level of 12,13-diHOME in a plasma sample from the human subject, wherein a plasma 12,13-diHOME level greater than a determined baseline level indicates BAT activation.

In certain embodiments, the invention features a method of determining whether a human subject has brown adipose tissue (BAT) activation, said method comprising determining the level of 12,13-diHOME in a plasma sample from the human subject, wherein a plasma 12,13-diHOME level of 0.2 pmol/mL or greater indicates BAT activation. Alternatively, a plasma 12,13-diHOME level of 0.2 nM or 200 pM or greater indicates BAT activation.

In one embodiment, the level of 12,13-diHOME is determined using mass spectrometry.

In one embodiment of the foregoing aspects, the subject has a metabolic disorder or heart disease. In some embodiments, the metabolic disorder is hyperlipidemia, insulin resistance, metabolic syndrome, obesity, and/or diabetes.

In one embodiment of the foregoing aspects, the human subject has at least one of the following characteristics: a plasma alanine transaminase (ALAT) level greater than 0.6 µkat/l; a Body Mass Index (BMI) 30 or more; a Homeostatic Model Assessment of Insulin Resistance (HOMA-IR) score of 1.9 or more; a plasma triglyceride level greater than 1.7 mmol/l; a plasma aspartate transaminase (ASAT) level of greater than 0.3 µkat/l for a male subject or a plasma ASAT level of greater than 0.6 µkat/l for a female subject; a plasma leptin level of 40 ng/ml or more; or a plasma gGT level of 0.9 µkat/l or greater for a male subject or a plasma gGT level of 0.6 µkat/l or greater for a female subject.

BRIEF DESCRIPTION OF THE DRAWINGS

FIG. 1A depicts a dendrogram of all lipids included in the initial screen according to their original fatty acid and enzymatic pathway. FIG. 1B depicts distribution of pro-inflammatory and anti-inflammatory lipid species for all lipid species measured by LC-MS/MS.

FIG. 2A depicts a volcano plot of 88 lipids comparing the fold induction after cold challenge to the p value (paired t-test). The dashed line indicates a p value of 0.05. 12,13-diHOME is marked by an arrow. n=9 individual subjects. FIG. 2B depicts individual patient plasma concentration of 12,13-diHOME before and after cold challenge. The p-value for a paired t-test is shown. FIG. 2C graphically depicts plasma 12,13-diHOME concentration plotted with BAT specific activity as measured by positron emission tomography (PET) scan of radiolabeled flurodeoxyglucose. R is the Spearman correlation between 12,13-diHOME and BAT activity. FIG. 2D-2I graphically depict circulating 12,13-diHOME concentration plotted against body mass index (BMI) (FIG. 2D), HOMA-IR (FIG. 2E), circulating triglycerides (FIG. 2F), circulating LDL-cholesterol (FIG. 2G), HDL-cholesterol (FIG. 2H), and circulating alanine transaminase (ALAT) (FIG. 2I). In each panel, R is the Spearman correlation between 12,13-diHOME and each circulating parameter. N=55 individual subjects (13M/42F). The p value shown was calculated using algorithm AS 89.

FIGS. 4A-4I depict circulating 12,13-diHOME concentration plotted against age (FIG. 4A), fasting plasma insulin (FPI) (FIG. 4B), fasting plasma glucose (FPG) (FIG. 4C), hemoglobin A1c (HbA1c) (FIG. 4D), C-reactive protein (CrP) (FIG. 4E), circulating leptin (FIG. 4F), circulating total cholesterol (FIG. 4G), circulating aspartate transaminase (ASAT) (FIG. 4H), and circulating gamma-glutamyl transpeptidase (gGT) (FIG. 4I). In each panel, R is the Spearman correlation coefficient and males are shown in blue while females are shown in pink. N=55 individual subjects (13 M/42 F). FIG. 4J depicts measurement of circulating 12,13-diHOME in each body mass index (BMI) category. Data are presented as normalized means±s.e.m.; n=15 lean, 13 overweight and 27 obese subjects. FIG. 4K depicts measurement of circulating 12,13-diHOME in each BMI category of males and females. Data are presented as normalized means±s.e.m.; n=15 lean (4 M/11 F), 13 overweight (4 M/9 F) and 27 obese subjects (5 M/22 F); *p<0.05 by t-test. FIG. 4L depicts measurement of circulating 12,13-diHOME in each BMI category of subjects with normal glucose tolerance (NGT) or Type 2 diabetes (T2D). Data are presented as normalized means±s.e.m.; n=15 lean, 13 overweight (10 NGT/3 T2D) and 27 obese subjects (20 NGT/7 T2D).

FIG. 5A depicts measurement of serum 12,13-diHOME concentration in control mice compared to animals treated with Norepinephrine (NE) for 30 minutes and animals exposed acutely to 4° C. cold for 1 hour. Data are means+/−s.e.m.; n=6 control mice, 7 NE treated, 7 cold exposed. *p<0.05, *p<0.005 by t-test. FIG. 5B depicts measurement of serum concentration of 12,13-diHOME in male and female mice after a 7 day cold challenge compared to mice housed in thermoneutral conditions. Data are means+/−s.e.m.; n=6 mice per group; *p<0.05 by t-test. FIG. 5C schematically represents the biosynthetic pathway of 12,13-diHOME production from linoleic acid. FIG. 5D depicts Ephx1 and Ephx2 mRNA expression measured by qPCR in BAT from control mice compared to animals exposed acutely to 4° C. cold for 1 hour. Data are means+/−s.e.m.; n=6 control mice, 7 cold exposed. *p<0.05 by t-test. FIG. 5E depicts Ephx1 gene expression measured by qPCR in BAT, sWAT, and eWAT from a separate cohort of mice housed at either thermoneutrality or cold for 7 days. Data are presented as normalized means±s.e.m.; n=4 per group; *p<0.05 by t-test. FIG. 5F depicts Ephx2 gene expression measured by qPCR in BAT, sWAT, and eWAT from a separate cohort of mice housed at either thermoneutrality or cold for 7 days. Data are presented as normalized means±s.e.m.; n=4 per group; *p<0.05 by t-test. FIG. 5G depicts measurement of 12,13-diHOME levels in media from BAT and sWAT cultured ex vivo for 1 hour normalized to tissue weight. Data are means+/−s.e.m.; n=6 mice; *p<0.05 by t-test. FIG. 5H depicts measurement of 12,13-diHOME concentrations in BAT from wild type and Myf5$^{cre}$BMPr1a$^{f/f}$ mice (KO) housed at cold or thermoneutrality for 2 or 11 days. Data are plotted as the normalized means±s.e.m.; n=5 WT thermoneutral males, 5 WT cold males, 4 KO thermoneutral males, 5 KO cold males, 3 WT thermoneutral females, 6 WT cold females, 4 KO thermoneutral females, 6 KO cold females; *p<0.05 by t-test.

FIG. 6A depicts 12,13-diHOME concentrations measured by LC-MS/MS in serum from wild type and Myf5$^{cre}$BMPr1a$^{f/f}$ mice (KO) housed at cold or thermoneutral for 2 or 11 days. Data are plotted as the normalized means±s.e.m.; n=5 WT thermoneutral males, 5 WT cold males, 4 KO thermoneutral males, 5 KO cold males, 3 WT thermoneutral females, 2 WT cold females, 4 KO thermoneutral females, 1 KO cold females; *p<0.05 by t-test. FIG. 6B depicts Ephx family gene expression measured by qPCR in different tissues from mice housed at cold or thermoneutrality for 7 days. Data are plotted as the means normalized to thermoneutrality±s.e.m.; n=8 per group; *p<0.05 by t-test. FIG. 6C depicts meta-analysis of 4 publically available BAT gene expression datasets from mice exposed to cold for different lengths of time for genes in the 12,13-diHOME biosynthetic pathway. The induction by cold of each gene after cold exposure is shown by increased fold change on the y axis. FIG. 6D depicts 12,13-diHOME levels measured in different mouse tissues. Data are means+/−s.e.m.; n=8 mice; *p<0.05, p<0.005, *p<0.0005 by t-test. FIG. 6E depicts 12,13-diHOME concentrations measured by LC-MS/MS in sWAT from wild type and Myf5$^{cre}$BMPr1a$^{f/f}$ mice (KO) housed at cold or thermoneutral for 2 or 11 days. Data are plotted as the normalized means±s.e.m.; n=5 WT thermoneutral males, 5 WT cold males, 4 KO thermoneutral males, 5 KO cold males, 3 WT thermoneutral females, 2 WT cold females, 4 KO thermoneutral females, 1 KO cold females; *p<0.05 by t-test. FIG. 6F depicts Ephx1 gene expression measured by qPCR in BAT and sWAT from mice treated daily with 1 mg/kg body weight CL316,243 intraperitoneally for 10 days. Data are presented as normalized means±s.e.m.; n=6 per group; *p<0.05 by t-test. FIG. 6G depicts Ephx2 gene expression measured by qPCR in BAT and sWAT from mice treated daily with 1 mg/kg body weight CL 316,243 intraperitoneally for 10 days. Data are presented as normalized means±s.e.m.; n=6 per group; *p<0.05 by t-test.

FIG. 7A graphically depicts body temperature in mice cold challenged at 4° C. for 90 min after pretreatment with 12,13-diHOME, 12,13-epOME or vehicle. Data are means±s.e.m.; n=5 per group; *p<0.05 12,13-diHOME vs. Vehicle by ANOVA with post-hoc Bonferroni test. FIGS. 7B and 7C depict total V(O$_2$) consumed and V(CO$_2$) produced (FIG. 7B) and average respiratory exchange ratio (R.E.R.) (FIG. 7C) measured by CLAMS for 1 h at cold (4° C.) in mice acutely treated with 12,13-diHOME or vehicle. FIG. 7D depicts measurement of serum triglyceride levels in mice fed HFD and treated with 12,13-diHOME or vehicle for 2 weeks. Data are means+/−s.e.m.; n=6 treated vs. 5 controls; *p<0.05 by t-test. FIG. 7E depicts measurement of radioactivity per 10 mg of tissues from mice treated with vehicle, Norepinephrine (NE) or 12,13-diHOME and then given a bolus of radiolabeled oleate. Tissues were measured by scintillation counting in liver, gastrocnemius muscle (Gastroc), soleus muscle, heart, BAT, sWAT and epididymal white adipose tissue (eWAT). Data are means±s.e.m.; n=8 per group; *p<0.05 12,13-diHOME vs. Vehicle by ANOVA with post-hoc Bonferroni test. FIG. 7F depicts representative images of luciferase activity in UCP1cre$^{+/−}$ Rosa(stop)Luc$^{+/−}$ injected intravenously with luciferin-conjugated fatty acid and 12,13-diHOME or vehicle. Data are representative images at 0, 10 and 55 min. FIG. 7G depicts quantification of luciferase activity represented in FIG. 7F. Luminescence was measured every 90 seconds. FIG. 7H depicts average of total luciferase counts from 6 individual experiments plotted as the normalized means±s.e.m.; n=6 per group; *p<0.05 12,13-diHOME vs. vehicle by t-test.

FIG. 8A depicts pulse measured in the tail after pretreatment with 12,13-diHOME or vehicle. Data are means±s.e.m.; n=6 per group. FIG. 8B depicts systolic pressure measured in the tail vein after pretreatment with 12,13-diHOME or vehicle. Data are means±s.e.m.; n=6 per group. FIG. 8C depicts diastolic pressure measured in the tail after pretreatment with 12,13-diHOME or vehicle. Data are means±s.e.m.; n=6 per group.

FIG. 9A depicts measurement of body weights over a 7-day course of daily injection treatment. Data are means+/−s.e.m.; n=6 treated vs. 5 controls. FIG. 9B graphically depicts glucose tolerance test of a separate cohort of diet-induced obesity mice treated every other day for 2 weeks with either 12,13-diHOME or vehicle. Data are means+/−s.e.m.; n=5 per group. FIG. 9C depicts measurement of serum non-esterified free fatty acids (FFA) of mice treated daily for one week with either 12,13-diHOME or vehicle. Data are means+/−s.e.m.; n=6 treated vs. 5 controls. FIG. 9D depicts mRNA expression measured by qPCR of UCP1 and LPL in tissue from mice treated every other day for two weeks with either 12,13-diHOME or vehicle. Data are means+/−s.e.m.; n=6 treated per group; *p<0.05 by t-test. FIG. 9E depicts oral lipid tolerance test showing serum triglyceride concentration from mice treated with vehicle or 12,13-diHOME and then given an oral bolus of triglyceride. Data are means±s.e.m.; n=6 per group; *p<0.05 by ANOVA with post-hoc Bonferroni test. FIG. 9F depicts measurement of radioactivity per 10 mg of tissues from mice treated with vehicle, Norepinephrine (NE) or 12,13-diHOME and then given a bolus of radiolabeled glucose. Tissues were measured by scintillation counting in liver, gastrocnemius muscle (Gastroc), soleus muscle, heart, BAT, sWAT, and epididymal white adipose tissue (eWAT). Data are means±s.e.m.; n=8 per group; *p<0.05 12,13-diHOME vs. Vehicle by ANOVA with post-hoc Bonferroni test. FIG. 9G depicts measurement of radioactivity per 10 mg of tissues from mice treated with vehicle or 12,13-diHOME and then given an oral bolus of radiolabeled triglyceride. Tissues were measured by scintillation counting in liver, Gastroc, soleus muscle, heart, BAT, sWAT, and eWAT. Data are means±s.e.m.; n=6 per group; *p<0.05 by t-test.

FIG. 10A graphically depicts fatty acid uptake in mature brown adipocytes constitutively expressing firefly luciferase that were pretreated with either 12,13-diHOME or vehicle measured by luciferase activity using 10 µM FFA-SS-Luc. Data are plotted as the normalized means±s.e.m.; n=6 wells per group; *p<0.05 12,13-diHOME vs. vehicle by ANOVA with post-hoc Bonferroni test. FIG. 10B depicts measurement of radiolabeled $^{14}$C palmitic acid uptake in mature brown adipocytes pretreated for 15 minutes with either 12,13-diHOME or vehicle. The data was normalized by protein content. Data are presented as means±s.e.m.; n=10-11 wells per group; *p<0.05 12,13-diHOME vs. vehicle by t-test. FIG. 10C depicts measurement of radiolabeled $^{14}$C palmitic acid oxidation in mature brown adipocytes pretreated with either 12,13-diHOME or vehicle. The data was normalized by protein content. Data are presented as means±s.e.m.; n=10-11 wells per group; p value is shown for 12,13-diHOME vs. vehicle by t-test. FIG. 10D depicts measurement of basal respiration of mature brown adipocytes treated with either 12,13-diHOME or vehicle. The data was normalized by protein content. Data are presented as means±s.e.m.; n=10-

11 wells per group; *p<0.05 12,13-diHOME vs. vehicle by t-test. FIG. 10E depicts western blot analysis of membrane and cytosol fractions of differentiated WT-1 brown adipocytes treated with 12,13-diHOME or vehicle. Fractionation of cellular compartments using differential centrifugation was confirmed using Tubulin as a marker of cytosol and Cadherin to mark the membrane. Densitometric measurement of the upper band corresponding to the oligomer form of FATP1 from immunoblots of three independent experiments is depicted in FIG. 10F. Data are presented as means±s.e.m.; n=3 separate experiments; *p<0.05 12,13-diHOME vs. vehicle by 1-way ANOVA. FIG. 10G depicts densitometric measurements of the low glycosylation form of CD36 from immunoblots of three independent experiments. Data are presented as means±s.e.m.; n=3 separate experiments; *p<0.05 12,13-diHOME vs. vehicle by 1-way ANOVA. FIG. 10H schematically represents a proposed model of 12,13-diHOME biosynthesis and action in cold activated BAT.

FIGS. 11A-11F depicts lipid profiling by LC-MS/MS in human plasma after saline or cold challenge.

DETAILED DESCRIPTION

Figure 1A:
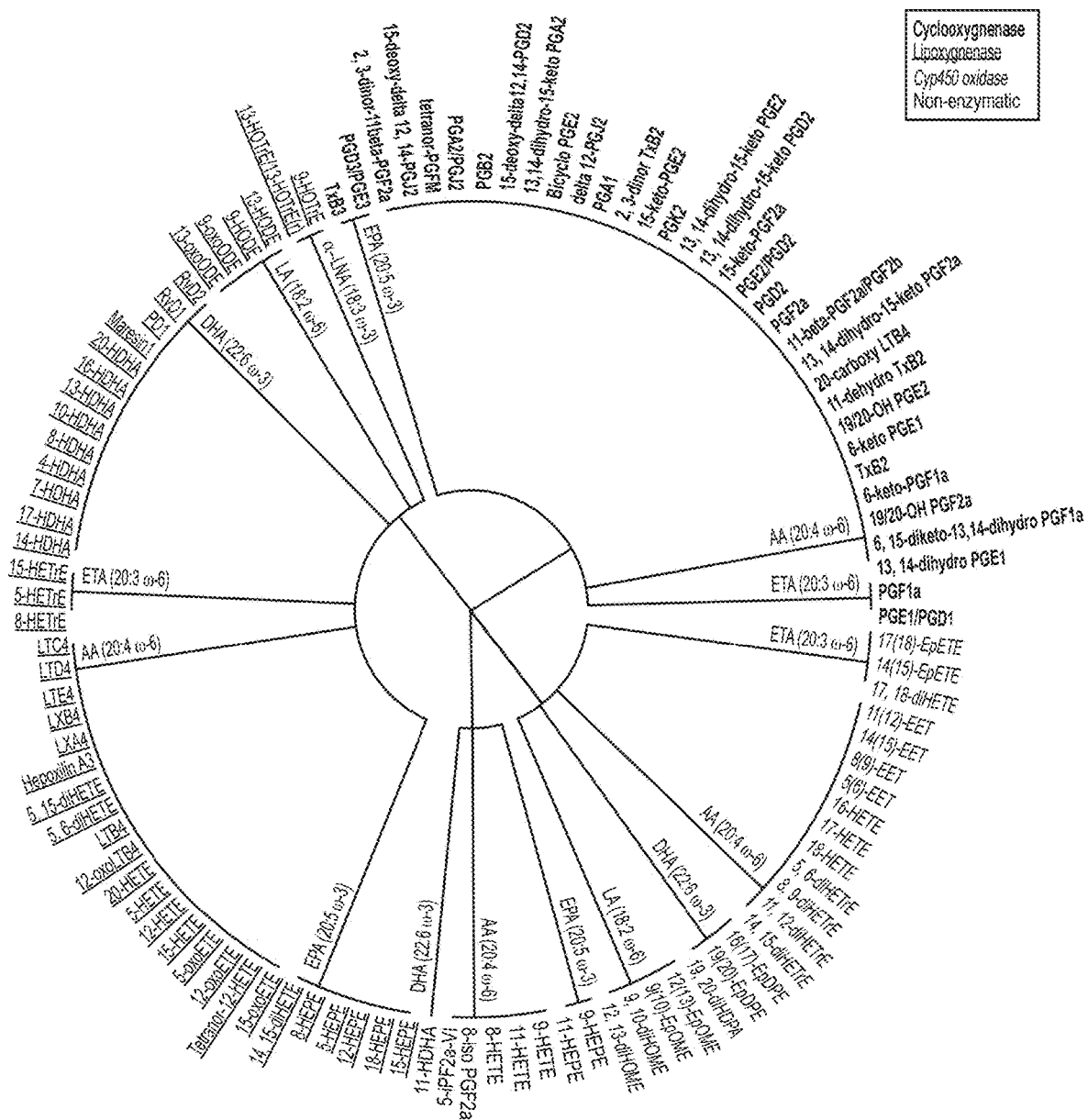
FIGS. 1A-1B depict annotation of lipid species profiled by LC-/MS in human and mouse serum and mouse adipose tissues.

The present invention provides, in one embodiment, methods and compositions for treating a subject having a disorder characterized by high level of lipids (e.g., fats, cholesterol and triglycerides) in the blood. Thus, the present invention provides, in certain embodiments, a method of treating a subject having a disorder or condition that would benefit from BAT activation e.g., a metabolic disorder such as hyperlipidemia, by administering 12,13-diHOME, to the subject. The present invention also provides, in one embodiment, administering 12,13-diHOME to a subject in order to decrease the level of circulating triglycerides in the blood of the subject in need thereof.

Definitions

In order that the present invention may be more readily understood, certain terms are first defined. Unless defined otherwise, technical and scientific terms used herein have the same meaning as is commonly understood by one of skill in the art. In addition, it should be noted that whenever a value or range of values of a parameter are recited, it is intended that values and ranges intermediate to the recited values are also intended to be part of this invention.

As used herein, the term "12,13-dihydroxy-9Z-octadecenoic acid" or "12,13-diHOME," refers to a long-chain fatty acid, which is a soluble epoxide hydrolase (sEH) metabolite of 12,13-EpOME. The structure of 12, 13-diHOME is described below (I).

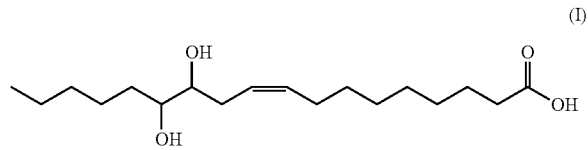 [SMILES: CCCCCC(O)C(O)C/C=C\CCCCCCCC(=O)O]

(I)

"Metabolic disorder" means a condition characterized by an alteration or disturbance in one or more metabolic processes in the body. Metabolic disorders include, but are not limited to, insulin resistance, diabetes (e.g., type 2 diabetes), obesity, metabolic syndrome, and hyperlipidemia.

"Metabolic syndrome" means a condition characterized by a clustering of lipid and non-lipid risk factors of metabolic origin. The risk factors place a subject at high risk for coronary artery disease. These conditions include Type II diabetes, central obesity also known as visceral adiposity, high blood pressure, and a poor lipid profile with elevated LDL ("bad") cholesterol, low HDL ("good") cholesterol, and elevated triglycerides.

As used herein, the term "hyperlipidemia" refers to a metabolic disorder characterized by abnormally elevated levels of any or all lipids and/or lipoproteins in the blood of a subject.

The term "a disorder associated with hyperlipidemia" refers to a disease or condition in which hyperlipidemia is considered a risk factor. Examples of disorders associated with hyperlipidemia include, but are not limited to, diabetes, obesity, heart disease, and atherosclerosis.

As used herein, the term "total cholesterol level" refers to a measure of the total amount of cholesterol in the blood, i.e., the combination of low-density lipoprotein (LDL) cholesterol level, high-density lipoprotein (HDL) cholesterol level, and triglyceride level.

As used herein, the term "triglyceride" refers to lipids that are composed of a glycerol esterified to 3 fatty acid chains of varying length and composition.

As used herein, the term "triglycerides in the circulation" or "circulating triglycerides" refers to triglycerides in the blood, plasma, or serum of a subject.

As used herein, the term "cardiovascular disease" or "heart disease" refers to a disease affecting the heart or blood vessels, which includes, for example, arteriosclerosis, coronary artery disease (or narrowing of the arteries), heart valve disease, arrhythmia, heart failure, hypertension, orthostatic hypotension, shock, endocarditis, diseases of the aorta and its branches, disorders of the peripheral vascular system, heart attack, cardiomyopathy, and congenital heart disease.

"Diabetes" or "diabetes mellitus" means a disease in which the body does not produce or properly use insulin, resulting in abnormally high blood glucose levels. In certain embodiments, diabetes is type 1 diabetes. In certain embodiments, diabetes is type 2 diabetes.

"Prediabetes" means a condition in which a subject's blood glucose levels are higher than in a subject with normal blood glucose levels but lower but not high enough for a diagnosis of diabetes.

"Type 2 diabetes" means diabetes characterized by insulin resistance and relative insulin deficiency (also known as diabetes mellitus type 2, and formerly called diabetes mellitus type 2, non-insulin-dependent diabetes (NIDDM), obesity related diabetes, or adult-onset diabetes).

"Obesity" means an excessively high amount of body fat or adipose tissue in relation to lean body mass. The amount of body fat (or adiposity) includes both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. "Overweight" refers to individuals with a BMI of 25 to 30, as defined by the Center for Disease Control and Prevention.

"Steatosis" means a condition characterized by the excessive accumulation of triglycerides in hepatocytes.

As used herein, the term "treating" a disease or disorder means reversing, alleviating, ameliorating, inhibiting, slowing down or stopping the progression, aggravation, deterioration, or severity of a condition associated with such a disease or disorder, but not necessarily requiring a complete treatment or prevention of the disease or disorder. In one embodiment, the symptoms of a disease or disorder are alleviated by at least 5%, at least 10%, at least 20%, at least 30%, at least 40%, at least 50%, or more than 50%.

The terms "prevent" or "preventing" refer to delaying or forestalling the onset or development of a disease, disorder, or condition for a period of time from minutes to indefinitely. Prevent also means reducing risk of developing a certain disease, disorder, or condition.

"At risk for developing" means a subject is predisposed to developing a condition or disease. In certain embodiments, a subject at risk for developing a condition or disease exhibits one or more symptoms of the condition or disease, but does not exhibit a sufficient number of symptoms to be diagnosed with the condition or disease. In certain embodiments, a subject at risk for developing a condition or disease exhibits one or more symptoms of the condition or disease, but to a lesser extent required to be diagnosed with the condition or disease.

The term "effective amount" or "effective dose", as used interchangeably herein, refers to any amount or dose of a compound or composition that is sufficient to fulfill its intended purpose(s), i.e., a desired biological or medicinal response in a tissue or subject at an acceptable benefit/risk ratio. In some embodiments, an "effective amount" is an amount that, when administered according to a particular regimen, produces a positive clinical outcome with a reasonably acceptable level of adverse effects (e.g., toxicity), such that the adverse effects, if present, are tolerable enough for a subject or patient to continue with the therapeutic regimen, and the benefit of the therapy overweighs risk of toxicity. In one embodiment, an effective amount is the amount of a compound that is able to decrease the plasma level of circulating triglycerides in a human subject relative to the level prior to administration of the compound.

The term "subject" refers to either a human or non-human animal. In one embodiment, a subject is a human subject. In another embodiment, the subject is a mammal.

By a "compound," is meant a chemical, be it naturally-occurring or artificially-derived. Compounds may include, for example, peptides, polypeptides, synthetic organic molecules, naturally-occurring organic molecules, nucleic acid molecules, and components or combinations thereof.

As used herein, "brown adipose tissue" or "BAT", refers to fat tissue characterized by multiple small lipid droplets and abundant mitochondria that oxidizes nutrients and generates heat. Central to the thermogenic activity of BAT is the expression of uncoupling protein 1 (UCP1).

By "increase in the level or activity" is meant a positive change in the amount or activity of a molecule (e.g., a biological marker) in a biological sample relative to a reference level or activity. The increase can be at least 5%, 10%, 25%, 50%, 75%, 80%, 100%, 200%, or even 500% or more over the level under control conditions. Similarly, a "decrease in the level or activity" is meant a negative change in the amount or activity of the molecule (e.g., a biological marker) in a biological sample relative to a reference level or activity.

The terms "sample" or "biological sample" as used herein include any biological specimen obtained from a subject. Samples may include, without limitation, whole blood, plasma, serum, red blood cells, white blood cells (e.g., peripheral blood mononuclear cells), saliva, urine, stool (i.e., feces), tears, sweat, sebum, nipple aspirate, ductal lavage, tumour exudates, synovial fluid, cerebrospinal fluid, lymph, fine needle aspirate, amniotic fluid, any other bodily fluid, cell lysates, cellular secretion products, inflammation fluid, semen and vaginal secretions. In preferred embodiments, the sample may be whole blood or a fractional component thereof such as, e.g., plasma, serum, or a cell pellet. Preferably the sample is readily obtainable by minimally invasive methods. Samples may also include tissue samples and biopsies, tissue homogenates and the like. In a preferred embodiment, the sample is a blood plasma sample.

The term "plasma" defines the colorless watery fluid of the blood that contains no cells, but in which the blood cells (erythrocytes, leukocytes, thrombocytes, etc.) are suspended, containing nutrients, sugars, proteins, minerals, enzymes, etc.

The term "quantity", "amount," or "level", as used interchangeably herein, refer to a detectable level of a biological marker, e.g., a protein, nucleic acid, lipid, or other compound in a biological sample. The terms as used herein may particularly refer to an absolute quantification of a molecule or an analyte in a sample, or to a relative quantification of a molecule or analyte in a sample, i.e., relative to another value such as relative to a reference value as taught herein, or to a range of values indicating a base-line expression of the biomarker. These values or ranges can be obtained from a single patient or from a group of patients. A level may be measured by methods known to one skilled in the art and also disclosed herein.

As used herein, the term "control level," "reference level" or "known standard level" refer to an accepted or predetermined level of a biological marker. For example, a control level of a marker may refer to a level determined or obtained before or prior to treatment with a therapeutic agent. Alternatively, a control level may refer to a level of a biological marker prior to the onset of disease or before administration of a drug. The level of a marker may be known in the art (e.g., normal level of HDL) or may be determined in reference to a certain subject. The level of a biological marker present in a subject or population of subjects having one or more particular characteristics, e.g., the presence or absence of a particular disease or condition.

Methods and Compositions for Treating Metabolic Disorders

Lipids called "lipokines" with signaling properties promoting insulin sensitivity and glucose tolerance have recently been identified (Cao, H., et al., *Cell.* 134, 933-944 (2008); Liu, S., et al., *Nature.* 502, 550-554 (2013); Yore, M. M., et al., *Cell.* 159, 318-332 (2014)). Brown adipocyte tissue (BAT) is a specialized lipid metabolic tissue linked to systemic metabolic homeostasis, and cold exposure activates substrate uptake and utilization in BAT in humans (Cypess, A. M., et al., *Proc. Natl. Acad Sci. U.S.A* 109, 10001-10005 (2012). No thermogenic lipokine has been identified that is linked to BAT activation or cold exposure, however, until the current identification of 12,13-dihydroxy-9Z-octadecenoic acid, as described in the examples below. Accordingly, the invention provides a novel therapeutic approach to BAT activation and BAT-specific lipid utilization using thermogenic lipokines.

The invention is based, at least in part, on the identification of 12,13-dihydroxy-9Z-octadecenoic acid (abbreviated 12, 13-diHOME) as an activator of brown adipose tissue (BAT). Specifically, 12, 13-diHOME increases fatty acid uptake and can reduce circulating triglycerides in a subject. The structure of 12, 13-diHOME is provided below in structure (I):

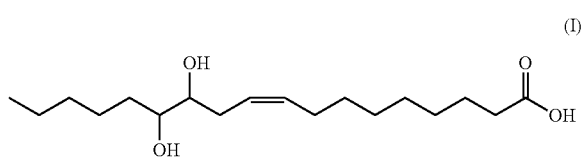 [SMILES: CCCCCC(O)C(O)C/C=C\CCCCCCCC(=O)O]

(I)

12,13-DiHOME is a component of the neutrophil oxidative burst. Biosynthesis of 12,13-diHOME and its isoform 9,10-dihydroxy-12Z-octadecenoic acid (9,10-diHOME) begins via formation of 12,13-EpOME or 9,10-EpOME epoxides from linoleic acid by Cytochrome P450 (Cyp) oxidases, followed by hydrolysis catalyzed by soluble epoxide hydrolases (sEH) to form the diols 12,13-diHOME and 9,10-diHOME, respectively (as described in FIG. 5C). Synthesis methods for 12,13-diHOME are known in the art (Kato et al. (1993) Bioscience, Biotechnology, and Biochemistry, vol. 57(2) pp. 283-287).

The compound described herein (12, 13-diHOME as shown in (I)) may exist in various stereoisomeric or tautomeric forms. Stereoisomers are compounds which differ only in their spatial arrangement. When a disclosed compound is named or depicted by structure without indicating stereochemistry, it is understood that the name or structure encompasses all possible stereoisomers, geometric isomers or a combination thereof.

Geometric isomers (also known as cis-trans isomerism or E-Z isomerism) are two or more coordination compounds which contain the same number and types of atoms, and bonds (i.e., the connectivity between atoms is the same), but which have different spatial arrangements of the atoms.

When a geometric isomer is depicted by name or structure, it is to be understood that the geometric isomeric purity of the named or depicted geometric isomer is at least 60%, 70%, 80%, 90%, 99% or 99.9% pure by weight. Geometric isomeric purity is determined by dividing the weight of the named or depicted geometric isomer in the mixture by the total weight of all of the geometric isomers in the mixture.

The compound described herein (12, 13-diHOME as shown in (I)) has two chiral centers. Thus, it may exist in diastereoisomeric forms. For each chiral center, it exists two enantiomeric forms and the present invention includes both enantiomers and mixtures of enantiomers, such as racemic mixtures.

Racemic mixture means 50% of one enantiomer and 50% of is corresponding enantiomer. The present teachings encompass all enantiomerically-pure, enantiomerically-enriched, diastereomerically pure, diastereomerically enriched, and racemic mixtures, and diastereomeric mixtures of the compounds described herein.

Enantiomeric and diastereomeric mixtures can be resolved into their component enantiomers or stereoisomers by well-known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

When a compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named and depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

Included in the present teachings are pharmaceutically acceptable salts of the compounds (12, 13-diHOME as shown in (I)) disclosed herein. Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts), alkaline earth metal salts (such as magnesium and calcium salts), lysine salts and arginine salts. These salts may be prepared by methods known to those skilled in the art.

As described herein, the present invention is based, at least in part, on the discovery that certain thermogenic lipokines, e.g., 12,13-diHOME activate fuel uptake by BAT. Thus, the level of circulating triglycerides in the blood of a subject can be decreased by administering an effective amount of 12,13-diHOME. In one embodiment, the invention provides a method of decreasing circulating levels of triglycerides in a subject in need thereof. High triglyceride levels can be associated with diabetes, kidney disease, and the use of some medications. A standard blood test can reveal whether a subject's triglycerides fall into a healthy range. Normal is defined as generally defined as being less than 150 milligrams per deciliter (mg/dL), or less than 1.7 millimoles per liter (mmol/L). Marginally high levels are considered 150 to 199 mg/dL (1.8 to 2.2 mmol/L), high levels are considered 200 to 499 mg/dL (2.3 to 5.6 mmol/L), and very high is considered 500 or more mg/dL. Thus, in one embodiment, an effective amount of 12,13-diHOME, a stereoisomer, a geometric isomer, or a pharmaceutically acceptable salt thereof, is administered to a subject having a triglyceride level over 150 mg/dL, such that the level of triglycerides in the subject is reduced to less than 150 mg/dL or is reduced at least 5%, at least 10%, at least 20%, at least 30%, at least 40%, or more than 40% of an initial level. Further, once the triglyceride level is reduced in a subject, 12,13-diHOME may be administered to a subject in need thereof in order to maintain a desired level of triglycerides.

Modulating the activity of BAT by modulating the levels of 12,13-diHOME can alter the level of circulating triglycerides in the blood of a subject, and serve to treat or prevent metabolic disorders, such as metabolic syndrome, hyperlipidemia and other diseases and conditions associated with elevated lipid levels. Further, modulating the activity of BAT by modulating the levels of 12,13-diHOME can increase thermogenesis in cells or tissue of a subject, and thereby serve to treat or prevent metabolic disorders that would benefit from increased energy consumption, e.g., obesity, diabetes, atherosclerosis, cardiovascular disease and metabolic syndrome.

In one embodiment, the invention provides a method of treating a subject having a disorder that would benefit from a decreased level of circulating triglycerides. Examples of a disorder that would benefit from decreased level of circulating triglycerides include, but are not limited to, hyperlipidemia, obesity, diabetes, atherosclerosis, heart disease, and metabolic syndrome. In one embodiment, methods of treating a disorder that would benefit from a decreased level of circulating triglycerides include decreasing the level of circulating triglycerides in a subject in need thereof by administering 12,13-diHOME to a subject in need thereof.

Metabolic Disorders

In one embodiment, the invention provides a method of treating a metabolic disorder comprising administering 12,13-diHOME to a subject in need thereof. Thus, the invention includes a method of treating a human subject having a metabolic disorder comprising administering an effective amount of 12,13-diHOME, a stereoisomer, a geometric isomer, or a pharmaceutically acceptable salt thereof, to a subject having a metabolic disorder.

Metabolic disorders are characterized by one or more abnormalities in metabolic function in the body. Metabolic disorders affect millions of people worldwide, and can be life-threatening disorders. Examples of metabolic disorders which may be treated using the methods and compositions disclosed herein include, but are not limited to, obesity, diabetes, metabolic syndrome, hyperlipidemia, disorders associated with hyperlipidemia, and insulin resistance. Thus, the methods and compositions of the invention may be used to treat a metabolic disorder by increasing energy consumption in cells or tissue of a subject in need thereof, attained through increasing thermogenesis by increasing BAT activity in the cells or tissue of the subject.

Metabolic Syndrome

In one embodiment, the invention provides a method of treating metabolic syndrome comprising administering 12,13-diHOME to a subject in need thereof. Thus, the invention includes a method of treating a human subject having metabolic syndrome comprising administering an effective amount of 12,13-diHOME, a stereoisomer, a geometric isomer, or a pharmaceutically acceptable salt thereof, to a subject having metabolic syndrome.

Metabolic syndrome is defined as a clustering of lipid and non-lipid cardiovascular risk factors of metabolic origin. The National Cholesterol Education Program (NCEP) Adult Treatment Panel m (ATIIII) established criteria for diagnosis of metabolic syndrome when three or more of five risk determinants are present. The five risk determinants are abdominal obesity (waist circumference of greater than 102 cm for men or greater than 88 cm for women), triglyceride levels greater than or equal to 150 mg/dL (or being on medicine to treat high triglycerides), a low HDL level (HDL cholesterol levels of less than 40 mg/dL for men and less than 50 mg/dL for women (or being on medicine to treat low HDL cholesterol), high blood pressure, i.e., blood pressure greater than or equal to 130/85 mm Hg (or being on medicine to treat high blood pressure), and high fasting glucose levels, i.e., levels greater than 100 mg/dL. These determinants can be readily measured in clinical practice (JAMA, 2001, 285: 2486-2497). The methods and compositions of the invention can be used to treat metabolic syndrome.

Hyperlipidemia

Hyperlipidemia is a disorder characterized by a high level of lipids (e.g., fats, cholesterol and triglycerides) in the blood. Blood tests are conducted to determine whether a subject has hyperlipidemia. Generally, hyperlipidemia is diagnosed using a blood test and determining whether the lipid and triglyceride levels of the subject are within a normal range, including determining the levels of any one of low density lipoprotein (LDL), high density lipoprotein (HDL), total cholesterol, and triglycerides. In one embodiment, hyperlipidemia is characterized as having at least one of the following as determined using a standard blood test for a subject: an LDL cholesterol level which is 130 mg/dL or more, an HDL cholesterol level which is 50 mg/dL or less, a total cholesterol level of 200 mg/dL or more, and a triglyceride level of 150 mg/dL or more.

In one embodiment, the subject having hyperlipidemia has a total cholesterol level of about 200 mg/dL to about 400 mg/dL or more. In one embodiment, the subject has a total cholesterol level greater than 200 mg/dL, greater than 210 mg/dL, greater than 220 mg/dL, greater than 230 mg/dL, greater than 240 mg/dL, greater than 250 mg/dL, greater than 260 mg/dL, greater than 270 mg/dL, greater than 280 mg/dL, or greater than 300 mg/dL.

In one embodiment, the subject having hyperlipidemia has a circulating triglyceride level greater than 150 mg/dL to about 500 mg/dL or more. In one embodiment, the subject has a circulating triglyceride level greater than 150 mg/dL, greater than 175 mg/dL, greater than 200 mg/dL, greater than 225 mg/dL, greater than 250 mg/dL, greater than 275 mg/dL, greater than 300 mg/dL, greater than 325 mg/dL, greater than 350 mg/dL, greater than 375 mg/dL, greater than 400 mg/dL, greater than 425 mg/dL, greater than 450 mg/dL, greater than 475 mg/dL, or greater than 500 mg/dL.

Hyperlipidemia can result from primary or secondary causes. Primary hyperlipidemia is generally caused by genetic defects, and secondary hyperlipidemia generally caused by secondary factors such as disease, drugs and/or dietary factors. Hyperlipidemia can also result from a combination of primary and secondary causes.

In one embodiment, the invention includes administering an effective amount of 12,13-diHOME to a subject having hyperlipidemia, wherein the effective amount of 12,13-diHOME is an amount that decreases the level of circulating triglycerides in the blood of the subject having hyperlipidemia relative to a level of circulating triglycerides prior to treatment of the subject with 12,13-diHOME or reducing the level by at least 5%. Alternatively, if the subject is already being treated and has achieved an improved level of circulating triglycerides, then 12,13-diHOME can be administered to maintain the reduced level of triglycerides.

In one embodiment, the invention provides a method of treating hyperlipidemia comprising administering 12, 13-diHOME to a subject in need thereof. Thus, the invention includes a method of treating a human subject having hyperlipidemia comprising administering an effective amount of 12,13-diHOME, a stereoisomer, a geometric isomer, or a pharmaceutically acceptable salt thereof, to the subject having hyperlipidemia.

In one embodiment, the invention includes administering 12,13-diHOME to a subject for treating a disorder associated with hyperlipidemia. Examples of disorders associated with hyperlipidemia include, but are not limited to, obesity, diabetes, atherosclerosis, and heart disease. Thus, the methods and compositions of the invention may be used to treat a cardiovascular disease, obesity, or atherosclerosis, by increasing energy consumption in cells or tissue of a subject, attained through increasing thermogenesis by increasing BAT activity in the cells or tissue of the subject.

Insulin Resistance

The methods and compositions described herein may also be used to treat a subject having insulin resistance. In one embodiment, the methods of the invention include treating a subject having insulin resistance by decreasing the level of circulating triglycerides in the blood of the subject by administering an effective amount of 12,13-diHOME to the subject.

One of the main functions of insulin is to lower blood glucose levels. A subject whose cells are sensitive to the effects of insulin needs only a relatively small amount of insulin to keep blood glucose levels in the normal range. A subject who is insulin resistant requires more insulin to get the same blood glucose-lowering effects. Insulin resistance may cause hyperinsulinemia. Hyperinsulinemia may be associated with high blood pressure, heart disease and heart failure, obesity (particularly abdominal obesity), osteoporosis, and certain types of cancer, such as colon, breast and prostate cancer.

Insulin resistance can be determined using common methods known in the art. For example, a glucose tolerance test, A1c test, and/or a lipid profile (measuring the HDL, LDL, triglycerides, and total cholesterol) of a subject may be used to determine if the subject has insulin resistance. In addition, a homeostatic model assessment (HOMA) of the subject may be performed to determine if the subject has insulin resistance. The HOME test involves measuring glucose and insulin levels and then using a calculation to estimate function of the beta cells in the pancreas that produce insulin and insulin sensitivity.

In one embodiment, the invention provides a method of treating insulin resistance comprising administering 12,13-diHOME to a subject in need thereof. Thus, the invention includes a method of treating a human subject having insulin resistance comprising administering an effective amount of 12,13-diHOME, a stereoisomer, a geometric isomer, or a pharmaceutically acceptable salt thereof, to a subject having insulin resistance.

Obesity

The methods and compositions described herein may also be used to treat a subject having obesity. In one embodiment, the methods of the invention include treating a subject having obesity by decreasing the level of circulating triglycerides in the blood of the subject by administering an effective amount of 12,13-diHOME to the subject.

Obesity is a condition characterized by an excessively high amount of body fat or adipose tissue in relation to lean body mass of a subject. The amount of body fat (or adiposity) includes both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. Overweight subject are considered having a BMI of 25 to 30, as defined by the Center for Disease Control and Prevention.

In one embodiment, methods and compositions of the invention may be used to treat obesity, by providing a means to control weight in the subject in need thereof by increasing energy consumption in cells or tissue of a subject, attained through increasing thermogenesis by increasing BAT activity in the cells or tissue of the subject.

Thus, 12,13-diHOME may be used to treat metabolic disorders, including insulin resistance, hyperlipidemia, diabetes, disorders associated with hyperlipidemia, obesity, and metabolic syndrome. In certain embodiments, the invention provides a method of preventing such disorders by administering 12,13-diHOME to a subject at risk for developing a metabolic disorder.

In one embodiment, the effective amount of 12,13-diHOME used to treat a metabolic disorder in a subject is an amount that decreases the level of circulating triglycerides in the blood of the subject relative to a level of circulating triglycerides prior to treatment of the subject with 12,13-diHOME. Alternatively, the effective amount may be an amount which maintains a desirable level of circulating triglycerides in the blood of a subject, e.g., maintains a level of less than 150 mg/dL of circulating triglycerides.

In one embodiment, administration of an effective amount of 12,13-diHOME may decrease the level or amount of circulating triglycerides in the blood of a subject by at least about 2-fold, 3-fold, 4-fold, 5-fold, 6-fold, 7-fold, 8-fold, 9-fold, 10-fold, 20-fold, 30-fold, 40-fold, 50-fold, 100-fold, 150-fold, 200-fold, 250-fold, 300-fold, 350-fold or 400-fold relative to a level of circulating triglycerides prior to treatment of the subject with 12,13-diHOME. Ranges within one or more of the preceding values e.g., about 2-fold to about 4-fold, about 3-fold to about 6-fold, about 5-fold to about 10-fold, about 8-fold to about 30-fold, about 20-fold to about 50-fold, about 40-fold to about 100-fold, about 50-fold to about 200-fold, about 200-fold to about 400-fold or about 2-fold to about 400-fold are contemplated by the invention.

Typical modes of administration of 12,13-diHOME include parenteral (e.g., intravenous, subcutaneous, intraperitoneal, intramuscular) injection or oral administration. In one embodiment, 12,13-diHOME is administered by injection. In another embodiment, the injection is subcutaneous. In a particular embodiment, the injection is into an adipose tissue.

In one embodiment, 12,13-diHOME is administered at a dose of about 0.5 mg/kg to about 300 mg/kg to a human subject. In one embodiment, 12,13-diHOME is administered at a dose of about 1 mg/kg, 2 mg/kg, 3 mg/kg, 4 mg/kg, 5 mg/kg, 10 mg/kg, 20 mg/kg, 30 mg/kg, 40 mg/kg, 50 mg/kg, 100 mg/kg, 150 mg/kg, 200 mg/kg, 250 mg/kg, 300 mg/kg, 350 mg/kg, 400 mg/kg, 450 mg/kg or 500 mg/kg. Ranges within one or more of the preceding values, e.g., about 1 mg/kg to about 5 mg/kg, about 2 mg/kg to about 10 mg/kg, about 6 mg/kg to about 40 mg/kg, about 20 mg/kg to about 100 mg/kg, about 50 mg/kg to about 200 mg/kg, about 100 mg/kg to about 400 mg/kg or about 1 mg/kg to about 500 mg/kg are contemplated by the invention.

In certain embodiments, 12,13-diHOME is administered to a subject in need thereof in combination with an additional therapeutic agent. For example, 12,13-diHOME can be administered to a subject in need in combination with a cholesterol lowering agent, such as a statin (e.g., Altoprev or Mevacor (lovastatin), Crestor (rosuvastatin), Lescol (fluvastatin), Lipitor (atorvastatin), Livalo (pitavastatin), Pravachol (pravastatin), and Zocor (simvastatin)), a bile acid binding drug (e.g., Colestid (colestipol), Prevalite (cholestyramine), and WelChol (colesevelam)), and/or a cholesterol absorption drug, (such as Zetia (ezetimibe)). In one embodiment, 12,13-diHOME is administered to a subject in need in combination with a triglyceride lowering agent, such as, but not limited to, a fibrate (e.g., Lopid (gemfibrozil), TriCor (fenofibrate)), an omega-3 fatty acid supplement, and niacin.

In addition, 12,13-diHOME may be administered in combination with a diabetic therapy and/or a HMG-CoA reductase inhibitor. Exemplary diabetic therapies are known in the art and include, for example, insulin sensitizers, such as biguanides (e.g., metformin) and thiazolidinediones (e.g., rosiglitazone, pioglitazone, troglitazone); secretagogues, such as the sulfonylureas (e.g., glyburide, glipizide, glimepiride, tolbutamide, acetohexamide, tolazamide, chlorpropamide, gliclazide, glycopyamide, gliquidone), the non-sulfonylurea secretagogues, e.g., meglitinide derivatives (e.g., repaglinide, nateglinide); the dipeptidyl peptidase IV inhibitors (e.g., sitagliptin, saxagliptin, linagliptin, vildagliptin, alogliptin, septagliptin); alpha-glucosidase inhibitors (e.g., acarbose, miglitol, voglibose); amylinomimetics (e.g., pramlintide acetate); incretin mimetics (e.g., exenatide, liraglutide, taspoglutide); insulin and its analogues (e.g., rapid acting, slow acting, and intermediate acting); bile acid sequestrants (e.g., colesevelam); and dopamine agonists (e.g., bromocriptine), alone or in combinations. Exemplary HMG-CoA reductase inhibitors include atorvastatin (Pfizer's Lipitor®/Tahor/Sortis/Torvast/Cardyl), pravastatin (Bristol-Myers Squibb's Pravachol, Sankyo's Mevalotin/Sanaprav), simvastatin (Merck's Zocor®/Sinvacor, Boehringer Ingelheim's Denan, Banyu's Lipovas), lovastatin (Merck's Mevacor/Mevinacor, Bexal's Lovastatina, Cepa; Schwarz Pharma's Liposcler), fluvastatin (Novartis' Lescol®/Locol/Lochol, Fujisawa's Cranoc, Solvay's Digaril), cerivastatin (Bayer's Lipobay/GlaxoSmithKline's Baycol), rosuvastatin (AstraZeneca's Crestor®), and pitivastatin (itavastatin/risivastatin) (Nissan Chemical, Kowa Kogyo, Sankyo, and Novartis).

In certain embodiments, the subject who is treated using the methods disclosed herein, is characterized as having a certain metabolic characteristic(s). As described below in the examples, certain metabolic indicators have been identified as having a negative correlation to plasma levels of 12,13-diHOME, including plasma triglyceride level, cholesterol level, plasma alanine transaminase (ALAT) level, Body Mass Index (BMI), Homeostatic Model Assessment of Insulin Resistance (HOMA-IR) score, plasma aspartate transaminase (ASAT) level, leptin level, and plasma gGT level. Alanine transaminase (ALAT) is also known in the art as alanine aminotransferase (ALT) or serum glutamic pyruvic transaminase (SGPT). Aspartate transaminase (ASAT) is also known in the art as aspartate aminotransferase (AST) or serum glutamic oxaloacetic transaminase (SGOT).

Methods for determining these metabolic characteristics are known in the art and can be used to identify subjects who would benefit from 12,13-diHOME therapy. In one embodiment, the methods and compositions disclosed herein are used to treat a human subject having a plasma triglyceride level greater than 1.7 mmol/1. Standard blood tests can be performed to determine a subject's plasma triglyceride level.

In one embodiment, the methods and compositions disclosed herein are used to treat a human subject having an ALAT level greater than 0.6 µkat/l. An alanine aminotransferase (ALT) or (ALAT) test, which is also know as serum glutamic pyruvic transaminase (SGPT) test, measures the amount of this enzyme in the blood and is a commonly used test to check liver function. ALAT is measured to determine if the liver of a subject is damaged or diseased. Low levels of ALAT are normally found in the blood. But when the liver is damaged or diseased, it releases ALAT into the bloodstream, which makes ALAT levels go up. Standard blood tests can be performed to determine a subject's ALAT level.

In one embodiment, the methods and compositions disclosed herein are used to treat a human subject having a BMI of 25 or more. In a separate embodiment, the methods and compositions disclosed herein are used to treat a human subject having a BMI of 30 or more (obese).

In one embodiment, the methods and compositions disclosed herein are used to treat a human subject having a HOMA-IR score of 1.9 or more. Homeostatic model assessment (HOMA) is a method for assessing β-cell function and insulin resistance (IR) from basal (fasting) glucose and insulin or C-peptide concentrations. HOME-IR scores are rated as follows: Healthy Range: 1.0 (0.5-1.4); Less than 1.0 means a subject is insulin-sensitive; above 1.9 indicates early insulin resistance; above 2.9 indicates significant insulin resistance. HOMA-IR is determined as follows: (fasting serum insulin (µU/ml)×fasting plasma glucose (mmol 1-1)/22.5) (Matthews et al. (1985) *Diabetologia*. 28: 412-419).

In one embodiment, the methods and compositions disclosed herein are used to treat a human subject having a plasma aspartate aminotransferase (ASAT) level of greater than 0.3 µkat/l for a male subject or a plasma ASAT level of greater than 0.6 µkat/l for a female subject. An aspartate aminotransferase (AST) or (ASAT) test, which is also known as serum glutamic oxaloacetic transaminase (SGOT) test, measures the amount of this enzyme in the blood and is a commonly used test to check liver function. ASAT is normally found in red blood cells, liver, heart, muscle tissue, pancreas, and kidneys. ASAT levels can be determined using standard methods known in the art.

In one embodiment, the methods and compositions disclosed herein are used to treat a human subject having a plasma gGT level of 0.9 µkat/l or greater for a male subject or a plasma gGT level of 0.6 µkat/l or greater for a female subject. gGT levels can be determined using a standard blood test, where the normal range for adults is 8 to 65 U/L.

In one embodiment, the methods and compositions disclosed herein are used to treat a human subject having a plasma leptin level of 40 ng/ml or more. In one embodiment, the subject is characterized as having leptin resistance. Leptin levels can be determined using standard blood testing methods known in the art.

Thus, in certain embodiments, 12, 13-diHOME is administered to a subject having a metabolic disorder who is also characterized as having at least one of the following characteristics: a plasma ALAT level greater than 0.6 µkat/l; a BMI of 30 or more; a HOMA-IR score of 1.9 or more; a plasma triglyceride level greater than 1.7 mmol/1; a plasma ASAT level of greater than 0.3 µkat/l for a male subject or a plasma ASAT level of greater than 0.6 µkat/l for a female subject; a plasma leptin level of 40 ng/ml or more; or a plasma gGT level of 0.9 µkat/l or greater for a male subject or a plasma gGT level of 0.6 µkat/l or greater for a female subject.

Pharmaceutical Formulations

Pharmaceutical formulations comprising 12,13-diHOME may be prepared according to methods known in the art to include physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as Tween™, Pluronics™ or polyethylene glycol (PEG).

The formulations to be used for in vivo administration must be sterile. This is readily accomplished by filtration through sterile filtration membranes.

Generally, the ingredients of compositions are supplied either separately or mixed together in unit dosage form, for example, as a dry lyophilized powder or water free concentrate in a hermetically sealed container such as an ampoule or sachet indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration. In an alternative embodiment, one or more of the pharmaceutical compositions of the invention is supplied in liquid form in a hermetically sealed container indicating the quantity and concentration of the agent.

The active agent can be incorporated into a pharmaceutical composition suitable for parenteral administration, typically prepared as an injectable solution. The injectable solution can be composed of either a liquid or lyophilized dosage form in a flint or amber vial, ampule or pre-filled syringe. The liquid or lyophilized dosage may further comprise a buffer (e.g., L-histidine, sodium succinate, sodium citrate, sodium phosphate or potassium phosphate, sodium chloride), a cryoprotectant (e.g., sucrose trehalose or lactose, a bulking agent (e.g., mannitol), a stabilizer (e.g., L-Methionine, glycine, arginine), an adjuvant (hyaluronidase).

The compositions of this invention may be in a variety of forms. These include, for example, liquid, semi-solid and solid dosage forms, such as liquid solutions (e.g., injectable and infusible solutions), microemulsion, dispersions, liposomes or suspensions, tablets, pills, powders, liposomes and suppositories.

The preferred form depends on the intended mode of administration and therapeutic application. Typical modes of administration include parenteral (e.g., intravenous, subcutaneous, intraperitoneal, intramuscular) injection or oral administration. In a preferred embodiment, 12,13-diHOME is administered by injection. In another embodiment, the injection is subcutaneous. In a particular embodiment, the administration is into adipose tissue.

The active ingredients may also be packaged in a microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Pharmaceutical compositions comprising an agent described herein may also be formulated for administration to a particular tissue. For example, in certain embodiments, it may be desirable to administer the agent into adipose tissue, either in a diffuse fashion or targeted to a site (e.g., subcutaneous adipose tissue).

12-13-diHOME as Marker for BAT Activation

The invention also features a novel method of determining the presence of BAT activation in a subject. As described in the examples below, standard methods for determining BAT activity in a subject involve radioactive fluorodeoxyglucose ($^{18}$F-FDG). The uptake of $^{18}$F-FDG by tissues is a marker for the tissue uptake of glucose, which in turn is closely correlated with certain types of tissue metabolism. After $^{18}$F-FDG is injected into a patient, a PET scanner can form two-dimensional or three-dimensional images of the distribution of $^{18}$F-FDG within the body. Thus, the current method for determining BAT activation is cumbersome as it involves injecting radioactive labels into a subject and requires radiology for evaluation.

Figure 2A:
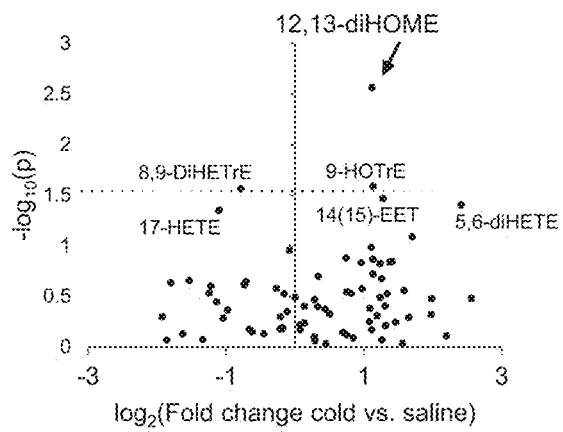
FIGS. 2A-2I depict identification of 12,13-diHOME, a cold-induced lipokine linked to BAT activation.
Figure 2B:
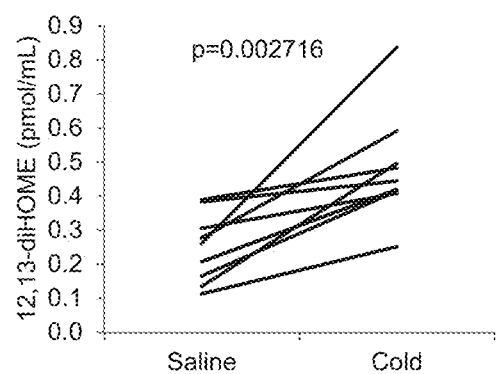
Figure 2C:
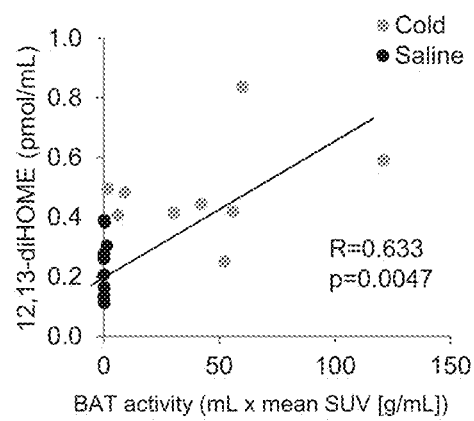
Figure 2D:
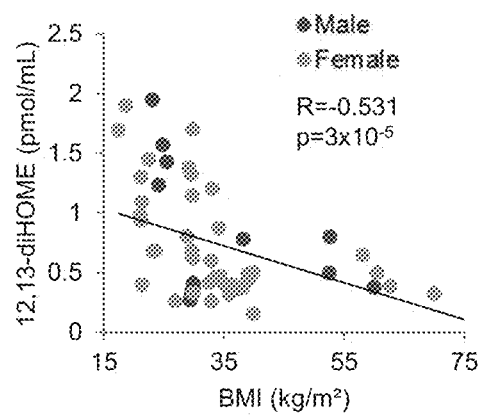
Figure 2E:
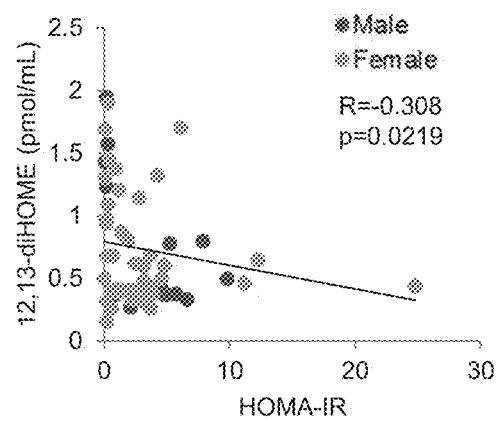

As described below in the examples, 12,13-diHOME can be used as a marker for determining whether a subject has BAT activation. As shown in FIG. 2C, plasma levels of 12,13-diHOME correlate with BAT activity in human subjects. Thus, BAT activity can be determined by measuring the level of 12,13-diHOME in the blood of a human subject. 12,13-diHOME presents an easier and more efficient way of determining BAT activation in comparison to the standard method which relies on $^{18}$F-FDG.

In one embodiment, the invention includes a method of detecting a 12,13-diHOME level in a human subject to determine whether the subject is undergoing BAT activation and, if so, at what level. The 12,13-diHOME level can be determined using a plasma sample obtained from a human subject. The 12,13-diHOME level in the sample is then determined using mass spectrometry. A plasma 12,13-diHOME level of 0.2 pmol/mL or greater in the sample indicates that BAT activation is occurring in the subject, and the level of activation can be correlated to the level of 12,13-diHOME level. Alternatively, a plasma 12,13-diHOME level of 0.2 nM or 200 pM or greater indicates BAT activation.

In certain embodiments, the invention features a method of determining whether a human subject has brown adipose tissue (BAT) activation, said method comprising determining the level of 12,13-diHOME in a plasma sample from the human subject, wherein a plasma 12,13-diHOME level greater than a determined baseline level indicates BAT activation.

The level of 12,13-diHOME in a subject may be of interest if the subject is undergoing treatment to activate BAT, wherein a baseline level of 12,13-diHOME can be determined prior to treatment in order to determine the efficacy of the treatment for activating BAT.

Mass spectrometric (MS) techniques can be used to determine the level of 12,13-diHOME in a sample from a subject, e.g., a plasma sample from a human subject. Detection and quantification of biomarkers by mass spectrometry may involve multiple reaction monitoring (MRM), such as described among others by Kuhn et al. 2004 (Proteomics 4: 1175-86). Mass spectrometry methods for lipids are described in Li et al. (2014) *Int. J. Mol. Sci.* 15:10492. Following MS, standard software for quantifying levels of 12, 13-diHOME are known in the art (see, for example, Materials and Methods described below in the examples).

In certain embodiments, BAT activation is determined using 12,13-diHOME levels in a subject who has heart disease or a metabolic disorder, such as, but not limited to, hyperlipidemia, insulin resistance, metabolic syndrome, obesity, and diabetes.

In certain embodiments, BAT activation is determined using 12,13-diHOME levels in a subject who has at least one of the following characteristics a plasma ALAT level greater than 0.6 μkat/l; a Body Mass Index (BMI) 30 or more; a HOMA-IR score of 1.9 or more; a plasma triglyceride level greater than 1.7 mmol/1; a plasma ASAT level of greater than 0.3 μkat/l for a male subject or a plasma ASAT level of greater than 0.6 µkat/l for a female subject; a plasma leptin level of 40 ng/ml or more; or a plasma gGT level of 0.9 µkat/l or greater for a male subject or a plasma gGT level of 0.6 µkat/l or greater for a female subject.

The invention also provides kits for the treatment and/or diagnosis of the disorders described above. Such kits include means for determining the level of 12,13-diHOME and instructions for use of the kit. For example, in particular embodiments, a kit of the invention includes means for determining the level of 12,13-diHOME. Kits of the invention can optionally contain additional components useful for performing the methods of the invention. For example, the kits may include means for obtaining and/or processing a biological sample from a subject. Means for isolating a biological sample from a subject can comprise one or more reagents that can be used to obtain a fluid or tissue from a subject, such as reagents that can be used to obtain or collect a cell or tissue sample from a subject. Means for processing a biological sample from a subject can include one or more reagents that can be used to transform a biological sample such that the level of one or more biomarkers in the sample can be determined. Such reagents can include, for example, reagents for isolating lipids from a biological sample. In preferred embodiments, the kits are designed for use with a human subject.

The invention is illustrated by the following examples, which are not intended to be limiting in any way.

EXAMPLES

The examples presented herein describe that certain thermogenic lipokines can act as novel indicators and mediators of BAT activity in response to cold. The examples were surprising in demonstrating that certain thermogenic lipokines, such as 12,13-dihydroxy-9Z-octadecenoic acid (12,13-diHOME), which is produced in response to cold, acutely activate fuel uptake by BAT and enhance cold tolerance, resulting in a decrease in the level of circulating triglycerides in the blood of a subject. The experiments exemplify novel methods and mechanisms of BAT activation and BAT-specific lipid utilization through 12,13-diHOME for use in treating, for example, metabolic disorders, such as obesity, diabetes, hyperlipidemia, or metabolic syndrome, by mimicking cold exposure. The studies described herein are also described in Lynes et al. (2017) *Nat Med* 23(5): 631.

Materials and Methods

The following methods described herein were used in the examples described below unless otherwise specified.

*In* Vitro Fatty Acid (FA) Uptake and FA Oxidation Assays

Stromal vascular cells were isolated from interscapular brown adipose tissue dissected from TgLuc mice (Stock no. 008450) obtained from The Jackson Laboratory. Cells were immortalized and differentiated into adipocytes in vitro according to the WT-1 protocol (Tseng, Y. H. et al., *Mol. Cell Biol.* 24, 1918-1929 (2004)). After 1 hour of serum starvation, mature adipocytes were treated with 1 µM 12,13-diHOME or methyl acetate vehicle in 0.1% w/v BSA in PBS for 15 minutes. After this treatment, cells were incubated with 10 µm FFA-SS-Luc (Intrace Medical) and imaged using the IVIS Spectrum CT using sequential 30 s exposures for 1 hour. Data was analyzed using Living Image Software and movies were assembled from individual images using ImageJ. All cultures were confirmed to be *Mycoplasma* free.

FA uptake and oxidation were determined by measuring both $^{14}C$-labeled palmitic acid uptake and conversion of $^{14}C$-labeled palmitic acid into $CO_2$. WT-1 brown preadipocytes were differentiated according to a standard adipogenic differentiation protocol for 9 days before cells were serum starved for 1 hour. Cells were treated with 1 µM 12,13-diHOME or methyl acetate vehicle in 0.1% w/v BSA in PBS for 15 minutes before the culture medium was removed, and cells were incubated with DMEM/H containing 4% FA-free BSA w/v in PBS, 0.5 mM palmitic acid, and 0.2 µCi/mL [1-$^{14}C$]-palmitic acid (PerkinElmer Life and Analytical Science, Waltham, Mass.) for 1 h. The incubation medium was transferred to a vial containing 1M acetic acid, capped quickly, and allowed to incubate for 1 h for $CO_2$ gas to be released. The $CO_2$ released was absorbed by hyamine hydroxide, and activity was counted. FA oxidation was calculated from $CO_2$ generated. To measure fatty acid uptake, cells were rinsed twice with PBS and lysed after incubation with [1-$^{14}C$]-palmitic acid. Lipids were extracted using a chloroform-methanol mixture (2:1), and $^{14}C$-counts were determined in the organic phase. Protein concentrations were determined by using the Pierce BCA kit (Life Technologies) according to instructions, and FA uptake ($^{14}C$ lipids in the cells) and oxidation ($^{14}CO_2$ generated) were normalized to protein content. All cells were confirmed to be *Mycoplasma* free.

Human Subjects

Human plasma was acquired from a previously performed cold exposure experiment approved by the Human Studies Institutional Review Boards of Beth Israel Deaconess Medical Center (Cypess, A. M., et al., *Proc. Natl. Acad Sci. U.S.A* 109, 10001-10005 (2012)). All subjects gave written informed consent before taking part in the study. Briefly, 9 healthy volunteers participated in 3 separate, independent study visits conducted in random order based on a Latin Square design. The night before the study day, the subjects were admitted to the clinical research center and began fasting from 12:00 AM onward. Room temperature was maintained above 23° C. throughout the stay in the clinical research center. Upon waking the next morning, the volunteers put on a standard hospital scrub suit. Depending on the study day, one of three stimuli was given: a single intramuscular dose of ephedrine 1 mg/kg; an equal volume of saline; or the volunteer was transported to a room set to 20° C. and donned a surgeon's cooling vest (Polar Products) with the water temperature set to 14° C. that was monitored by a digital thermometer (Fisher Scientific). Sixty minutes after the injection of ephedrine, saline, or the initiation of cold exposure, blood was drawn for measurement of lipid levels, and then an intravenous bolus of 440 MBq (12 mCi) of $^{18}F$-FDG was administered. 60 min after the $^{18}F$-FDG injection, images were acquired using a Discovery LS multidetector helical PET-CT scanner (GE Medical Systems). BAT mass and activity were both quantified using the PET-CT Viewer shareware.

For the second cohort of human subjects, 55 individuals were selected from the Leipzig biobank (42 women, 13 men) to represent a wide range of body mass index (BMI: 17.5-75.4 kg/m$^2$), categories of lean (BMI<25 kg/m$^2$; n=15; 4 M/11 F), overweight (BMI 25.1-29.9 kg/m$^2$; n=13; 4 M/9 F) or obese (BMI>30 kg/m$^2$; n=27; 5 M/22 F) and glucose metabolism parameters (fasting plasma glucose 3.9-13.4 mmol/1; fasting plasma insulin 3.8-451 pmol/1, HOMA-IR: 0.1-25). In the subgroup of lean, all individuals were normal glucose tolerant (NGT), whereas in the overweight subgroup, 10 individuals with NGT and 3 with type 2 diabetes (T2D) and in the obese group 20 NGT and 7 T2D patients were included. Phenotyping, definition of NGT and T2D as well as analyses of serum/plasma parameters (fasting plasma insulin (FPI), fasting plasma glucose (FPG), hemoglobin A1c (HbA1c), C-reactive protein (CrP), leptin, total cholesterol, aspartate transaminase (ASAT), and gamma-glutamyl transpeptidase (gGT) serum concentrations) were performed as described previously (Kloting, N., et al., Am J Physiol Endocrinol Metab. 299, E506-515 (2010)). The collection of human biomaterial, serum analyses and phenotyping were approved by ethics committee of the University of Leipzig (approval numbers: 159-12-21052012 and 017-12-23012012) and all subjects gave written informed consent before taking part in the study.

Lipidomic Profiling and 12,13-diHOME Quantification

All lipid standards were purchased from Cayman Chemical Company, Avanti Polar Lipids, or Santa Cruz Biotechnology, Inc. $C_{18}$SPE cartridges were purchased from Biotage. All solvents are of HPLC or LC-MS/MS grade and were acquired from Sigma-Aldrich, Fisher Scientific, or VWR International. Tissue samples were homogenized in 0.1×PBS in Omni homogenizing tubes with ceramic beads at 4° C. Aliquots of 100 µL serum or 1 mg protein of homogenized tissue (measured by BCA) were taken, depending on the experiment. A mixture of deuterium-labeled internal standards was added to each aliquot, followed by 3× volume of sample of cold methanol (MeOH). Samples were vortexed for 5 min and stored at −20° C. overnight. Cold samples were centrifuged at 14,000 g for 10 min, and the supernatant was then transferred to a new tube and 3 mL of acidified $H_2O$ (pH 3.5) was added to each sample prior to $C_{18}$ SPE and performed as previously described (Powell, W. S., Methods Mol Biol. 120, 11-24 (1999)). The methyl formate fractions were collected, dried under nitrogen, and reconstituted in 50 µL MeOH:$H_2O$ (1:1, by vol). Samples were transferred to 0.5 mL tubes and centrifuged at 20,000 g at 4° C. for 10 min. Thirty-five microliters of supernatant was transferred to LC-MS/MS vials for analysis using the BERG LC-MS/MS mediator lipidomics platform. Separation of signaling lipids was performed on an Ekspert MicroLC 200 system (Eksigent Technologies) with a Synergi™ Fusion-RP capillary $C_{18}$ column (150×0.5 mm, 4 µm; Phenomenex Inc.) heated to 40° C. A sample volume of 10 µL was injected at a flow rate of 20 µL/min. Lipids were separated using mobile phases A (100% $H_2O$, 0.1% acetic acid) and B (100% MeOH, 0.1% acetic acid) with a gradient starting at 60% B for 0.5 min, steadily increasing to 80% B by 5 min, reaching 95% B by 9 min, holding for 1 min, and then decreasing to 60% B by 12 min. MS analysis was performed on a SCIEX TripleTOF® 5600+ system using the HR-MRM strategy consisting of a TOF MS experiment looped with multiple MS/MS experiments. MS spectra were acquired in high-resolution mode (>30,000) using a 100-ms accumulation time per spectrum. Full-scan MS/MS was acquired in high sensitivity mode, with an accumulation time optimized per cycle. Collision energy was set using rolling collision energy with a spread of 15V. The identity of a component was confirmed using PeakView® software (SCIEX), and quantification was performed using MultiQuant™ software (SCIEX). The quantification of 12,13-diHOME was performed against a standard calibration curve built with 5 points ranging from 0.01 pg/µL to 100 pg/µL. Obtained values were corrected with the corresponding internal standard $d_4$-9,10-diHOME.

Mice and Treatments

All animal procedures were approved by the Institutional Animal Use and Care Committee at Joslin Diabetes Center and Harvard T.H. Chan School of Public Health. The experiments were not randomized. No statistical method was used to predetermine animal's sample size. For the cold exposure experiments, radiolabeled FA uptake experiment, and diet-induced obesity experiment, 12 week old male C57BL/6J mice (Stock no. 000664) were purchased from The Jackson Laboratory. For acute BAT activation, mice were either sacrificed as control animals, treated with NE for 30 minutes, or placed at 4° C. for 1 hour, then sacrificed for serum and tissue collection. In chronic cold exposures, transgenic mice carrying floxed alleles for the BMP receptor 1A were used to generate conditional gene deletions mouse models by intercrossing with Myf5-driven cre recombinase and compared to cre-negative littermate controls as described previously (Schulz, T. J., et al., Nature. 495, 379-383 (2013)). In addition to C57BL/6J mice, these transgenic animals were used for all chronic cold exposure experiments, with mice 10-18 weeks of age housed in a temperature controlled diurnal incubator (Caron Products & Services Inc.) at either 4° C. (cold) or 30° C. (thermoneutrality) on a 12 hour light/dark cycle. In all experiments, interscapular BAT, inguinal sWAT, and serum were dissected after sacrifice.

For ex vivo tissue incubation experiments, interscapular BAT and inguinal sWAT were dissected from 12 week old male C57BL/6J mice and incubated at 37° C. in Krebs solution for 1 hour, after which the tissue was discarded and LC-MS/MS was performed on the conditioned Krebs solution.

For cold tolerance assay, mice were injected retro-orbitally with 1 µg/kg body weight 12,13-diHOME (purchased from Cayman Chemical Company) in 0.1% w/v BSA in PBS or vehicle, then immediately placed in a cold room maintained at 4° C. and body core temperature was determined by rectal probe measurements. Mice injected retro-orbitally were also used to measure blood pressure and pulse with the tail cuff method (Hatteras Instruments).

For in vivo fatty acid organ distribution studies, an oleate/$^3$H-oleate tracer mix was complexed to fatty acid-free BSA (Schlein, et al., Cell Metab. 23, 441-453 (2016)) and injected into the tail vein of wild type C57BL/6J mice 15 minutes after treatment with either vehicle, 1 µg/kg body weight 12,13-diHOME in 0.1% BSA PBS or NE. Similarly, radiolabeled organ distribution studies were performed in mice either by injection into the tail vein with 2-desoxy-D-[$^{14}$C]-glucose (PerkinElmer, 0.025 mCi per kg) in PBS or orally gavaged with 10 mL/kg olive oil (Sigma) containing [9,10-$^3$H(N)]-triolein (PerkinElmer, 0.3 mCi/kg). In all assays, organs were harvested after 15 minutes under terminal anesthesia and systemic perfusion with PBS-heparin (10 U/ml) via the left heart ventricle. Tissues were homogenized by using Solvable (PerkinElmer) and disintegrations per minute per organ data were calculated by scintillation counting.

For in vivo bioluminescent fatty acid uptake experiments, UCP1cre$^{+/-}$ mice (Stock no. 024670) were bred with Rosa (stop)Luc$^{+/+}$ (Stock no. 005125), both obtained from The Jackson Laboratory. Male offspring carrying the UCP1-cre allele were injected retro-orbitally with 1 ug/kg body weight 12,13-diHOME in 0.1% BSA PBS or vehicle, and all mice were co-injected with 2 µm FFA-SS-Luc (Intrace Medical). Mice were anesthetized with isofluorane and imaged using the IVIS Spectrum CT using sequential 30 s exposures for 1 hour. Data was analyzed using Living Image Software and movies were assembled from individual images using ImageJ.

For CLAMS studies, mice were injected intravenously with 1 µg/kg body weight 12,13-diHOME in 0.1% BSA PBS or vehicle and then monitored using the CLAMS system in cold conditions (4° C.) for 1 hour. Respiratory exchange ratio (R.E.R.) was calculated as the ratio of total carbon dioxide produced to total oxygen consumed.

For the experiments with daily injections of 12,13-diHOME, mice were fed with a high-fat diet containing 60 kcal % fat (Research Diets Stock no. D12492) for 16 weeks prior to treatment and during the course of the experiment. Mice were first injected intraperitoneally daily with 1 ug/kg body weight, 12,13-diHOME in 0.1% BSA w/v in PBS or vehicle and body for one week, then injected every day with 10 ug/kg body weight two weeks. For all experiments, serum was collected and triglycerides were measured using a standard enzymatic assay (ZenBiosystems). Non-esterified FA were also measured with a colorimetric assay (Wako Chemicals USA). High-density and low-density lipoprotein fractions were isolated and cholesterol was measured with a colorimetric assay (Abcam). All mice were allowed ad libitum access to water and food.

Membrane Fractionation

WT-1 brown preadipocytes were differentiated according to a standard adipogenic differentiation protocol for 9 days before cells were serum starved for 1 hour. Cells were treated with 1 µM 12,13-diHOME or methyl acetate vehicle in 0.1% BSA w/v in PBS for 15 minutes before cells were scraped from tissue culture plates into homogenization buffer and membranes were separated according to previously published protocols (Nishiumi, S. & Ashida, H., *Bioscience, biotechnology, and biochemistry.* 71, 2343-2346 (2007)). Protein lysates were stored at −20° C. until further use. Protein concentrations were determined by using the Pierce BCA kit (Life Technologies) according to instructions. For immunoblots, lysates were diluted into Laemmli buffer and boiled, then loaded onto 10% Tris gels for SDS-PAGE. After complete separation of the proteins, these were transferred on a PVDF membrane (Amersham Biosciences), blocked in western blocking buffer (Roche), and primary antibodies listed in Table 1, below, were applied in blocking buffer over night at 4° C. After washing 4× for 15 min with TBS-T, secondary antibodies were applied for 1 h in blocking buffer. Membranes were washed again 3× times for 15 min in TBS-T and developed using chemiluminescence (ThermoFisher). After scanning films, densitometry was analyzed using ImageJ software.

TABLE 1

| Antibody List | Vendor | Catalog # |
|---|---|---|
| FATP1(ALSVL5, m-100) | Santa Cruz Biotechnology | sc-25541 |
| Pan-Cadherin(H-300) | Santa Cruz Biotechnology | sc-10733 |
| β-Tubulin | Cell Signaling Technology | 2146 |
| HRP conjugated anti Rabbit IgG | Cell Signaling Technology | 7074 |
| Anti-CD36 | Santa Cruz Biotechnology | sc-9154 | mRNA Expression

Total RNA was extracted from tissue with Trizol and purified using a spin column kit (Zymo Research). RNA (500 ng-1 µg) was reverse transcribed with a high-capacity complementary DNA (cDNA) reverse transcription kit (Applied Biosystems). Real-time PCR was performed in mouse tissues starting with 10 ng of cDNA and forward and reverse oligonucleotide primers (300 nM each) in a final volume of 10 µl with SYBR green PCR Master Mix (Roche). Fluorescence was determined and analyzed in an ABI Prism 7900 sequence detection system (Applied Biosystems). Acidic ribosomal phosphoprotein P0 (ARBP) expression was used to normalize gene expression. Real time PCR primer sequences are listed in Table 2, below.

TABLE 2

| Primer | Sequence | Gene |
|---|---|---|
| ARBPfor | TTTGGGCATCACCACGAAAA | ARBP |
| ARBPrev | GGACACCCTCCAGAAAGCGA | |
| Ephx1for | GGAGACCTTACCACTTGAAGATG | Ephx1 |
| Ephx1rev | GCCCGGAACCTATCTATCCTCT | |
| Ephx2for | ACCACTCATGGATGAAAGCTACA | Ephx2 |
| Ephx2rev | TCAGGTAGATTGGCTCCACAG | |
| Ephx3for | CAGTGGACTCCGATAGCACG | Ephx3 |
| Ephx3rev | TGGGACGACTACAGAGCCG | |
| Ephx4for | TCCCTGGTGTACGGCTACTG | Ephx4 |
| Ephx4rev | ATCTTAACCCGGAGTCCTTGA | |
| UCP1for | AGGCTTCCAGTACCATTAGGT | UCP1 |
| UCP1rev | CTGAGTGAGGCAAAGCTGATTT | |
| LPLfor | GCCCAGCAACATTATCCAGT | LPL |
| LPLrev | GGTCAGACTTCCTGCTACGC | |

The above sequences are set forth as SEQ ID Nos: 1 to 14 as follows: SEQ ID NO: 1 TTTGGGCATCACCACGAAAA; SEQ ID NO: 2 GGACACCCTCCAGAAAGCGA; SEQ ID NO: 3 GGAGACCTTACCACTTGAAGATG; SEQ ID NO: 4 GCCCGGAACC TATCTATCCT CT; SEQ ID NO: 5 ACCACTCATG GATGAAAGCTACA; SEQ ID NO: 6 TCAGGTAGAT TGGCTCCACAG; SEQ ID NO: 7 CAGTGGACTCCGATAGCACG; SEQ ID NO: 8 TGGGA CGACTACAGAGCCG; SEQ ID NO: 9 TCCCTG GTGTACGGCTACTG; SEQ ID NO: 10 ATCTTAACCCGGAGTCCTTG A; SEQ ID NO: 11 AGGCTTCCAGTACCATTAGGT; SEQ ID NO: 12 CTGAGTGAGGCA AAGCTGAT TT; SEQ ID NO: 13 GCCCAGCAAC ATTATCCAGT; SEQ ID NO: 14 GGTCAGACTTCCTGCTACGC.

Seahorse Bioanalyzer

WT-1 brown preadipocytes were seeded onto gelatin coated Seahorse Plates and differentiated according to standard protocols. Cells were starved for 1 h, then treated for 15 min with 1 µM 12,13-diHOME or methyl acetate vehicle. The oxygen consumption rates (OCR) were monitored in 200 µM palmitic acid plus 100 µM albumin in a Seahorse XF24 instrument using the standard protocol of 3 min mix, 2 min wait, and 3 min measure. For the normalization of respiration to protein content, cells were lysed in RIPA buffer and protein concentration was measured using the Pierce BCA kit (Life Technologies).

Statistics

No statistical method was used to predetermine sample size. All experiments were not blinded. All statistics were calculated using Microsoft Excel, Graphpad Prism and RStudio. For consistency, the Spearman correlation coefficient is shown however all Pearson and Kendall coefficients reached similar levels of significance. For all correlation coefficients, p value was calculated using algorithm AS 89 (Best, D. J. & Roberts, D. E., *Applied Statistics* 24, 377-379 (1975)).

Figure 1B:
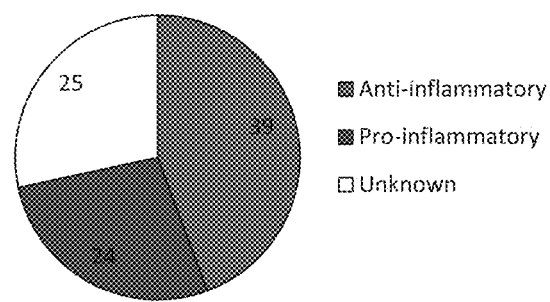

Example 1. Identification of 12,13-diHOME, a Cold-Induced Lipokine Linked to BAT Activation Cold exposure activates substrate uptake and utilization in BAT in as little as one hour in humans (Cypess, A. M., et al., *Proc. Natl. Acad Sci. U.S.A* 109, 10001-10005 (2012)). Lipokines can have effects on improving metabolism similar to cold exposure (Oh, D. Y., et al., *Cell.* 142, 687-698 (2010)). To identify thermogenic lipokines linked to BAT activation that may increase in subjects exposed to a cold challenge, liquid chromatography tandem mass spectrometry (LC-MS/MS) was used to measure the concentrations of a panel of 88 lipids with annotated signaling properties in the plasma of human volunteers exposed to cold (Cypess, A. M., et al., *Proc. Natl. Acad Sci. U.S.A* 109, 10001-10005 (2012)) (FIGS. 1A, 1B, and 11).

Figure 3:
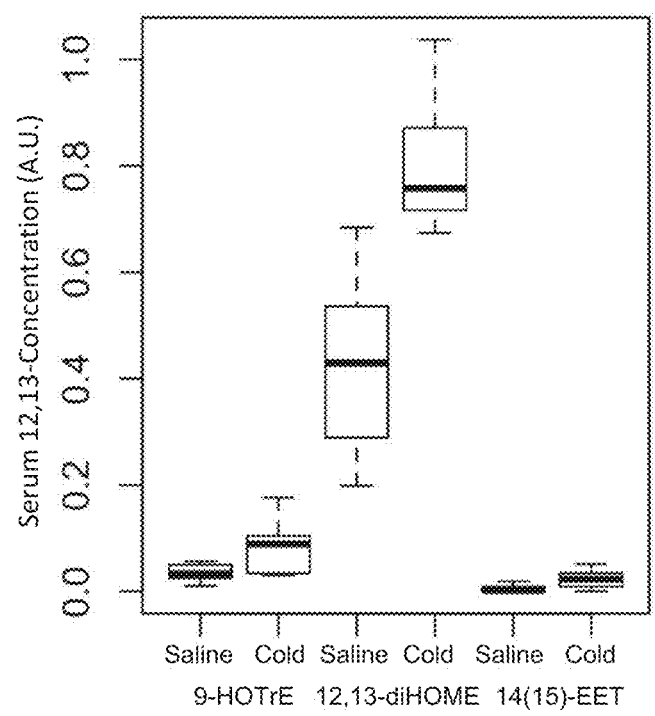
FIG. 3 depicts that levels of lipid species changed by a one-hour cold challenge. The difference in abundance of three lipid species reached a nominal p value of 0.05 after cold exposure. The two species with lower significance were only detectable after cold exposure.

This approach to identify putative lipokines is highly sensitive and covered a broad range of oxidized fatty acid metabolites. Notably, 3 species were significantly changed by cold in human circulation after 1 hour of cold challenge (FIG. 2A and FIG. 3). The lipid 12,13-diHOME, however, was the only species that increased in all subjects measured (FIG. 2B) and 12,13-diHOME levels correlated significantly to BAT activity measured by radiolabeled glucose uptake (FIG. 2C). 12, 13-diHOME was also significantly induced by cold in mice.

Figure 2F:
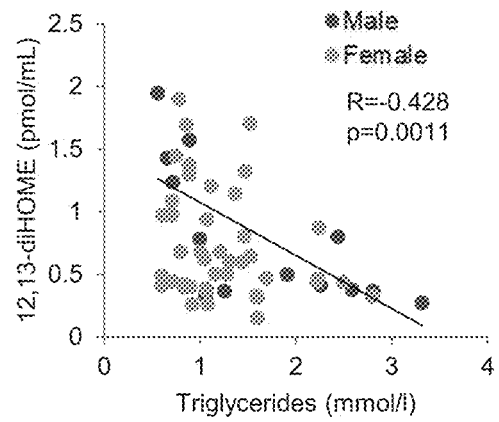
Figure 2G:
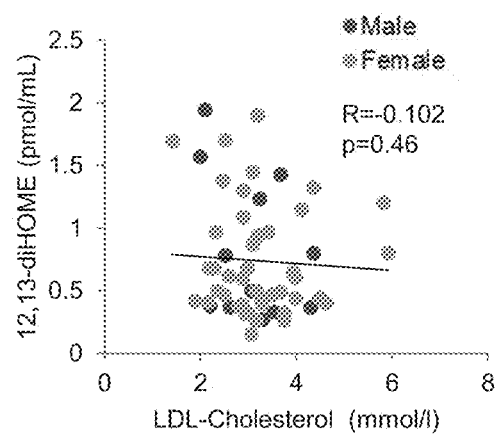
Figure 2H:
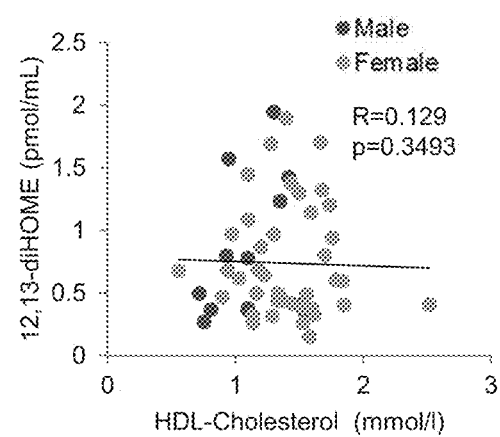
Figure 2I:
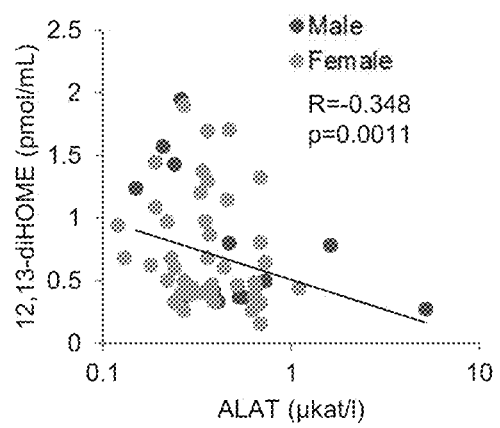
Figure 4A:
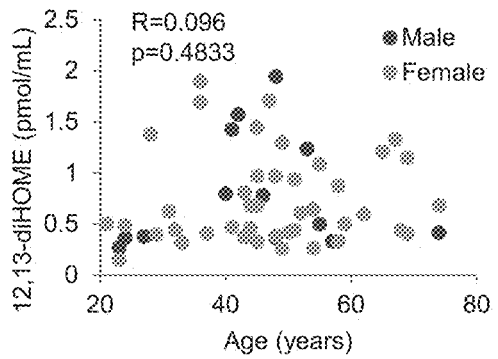
FIGS. 4A-4L depict anthropometric correlation of 12,13-diHOME.
Figure 4B:
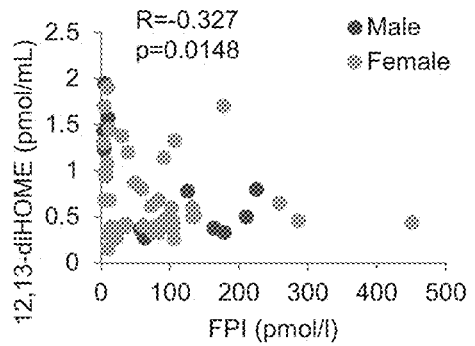
Figure 4C:
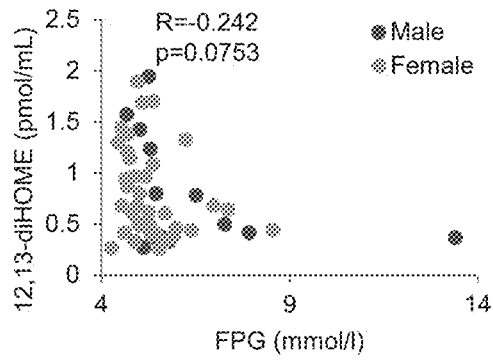
Figure 4D:
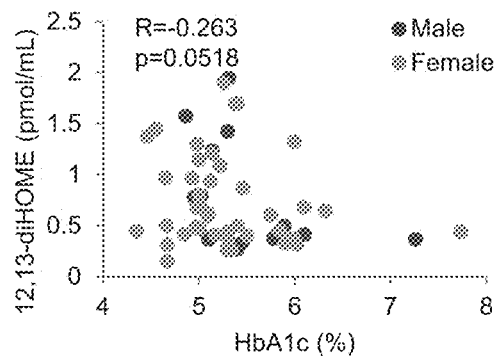
Figure 4E:
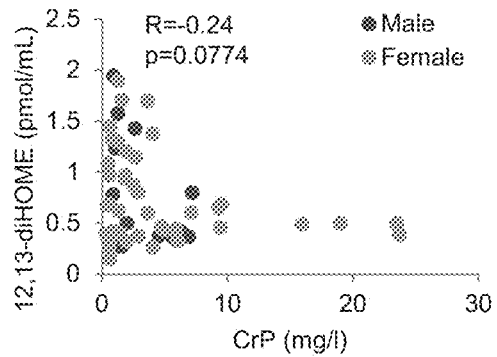
Figure 4F:
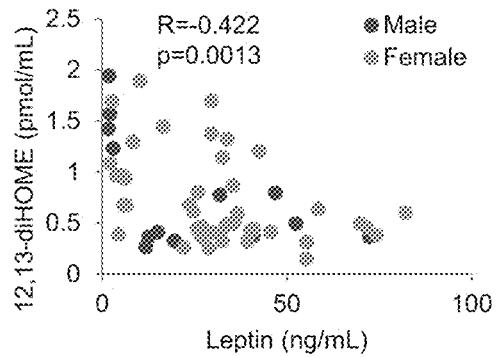
Figure 4G:
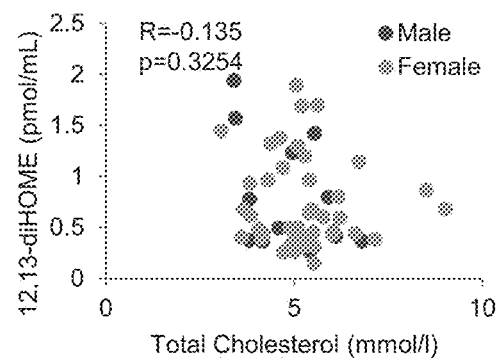
Figure 4H:
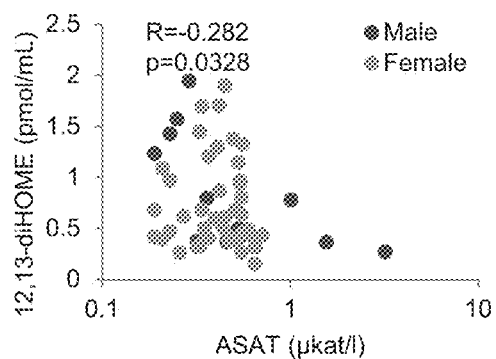
Figure 4I:
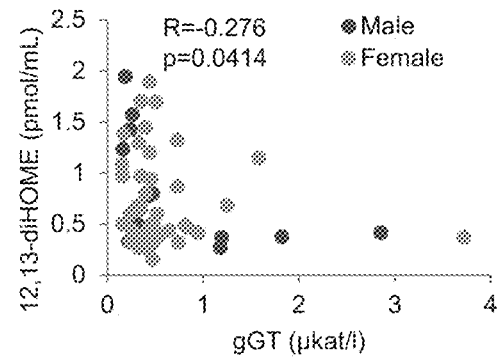
Figure 4J:
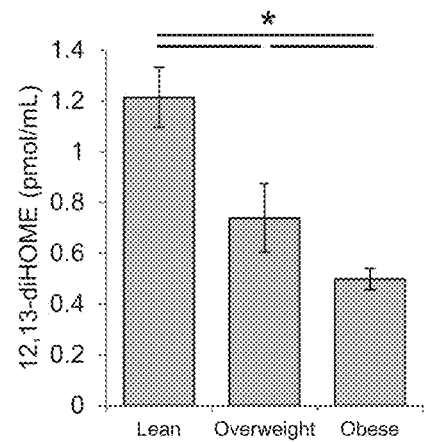
Figure 4K:
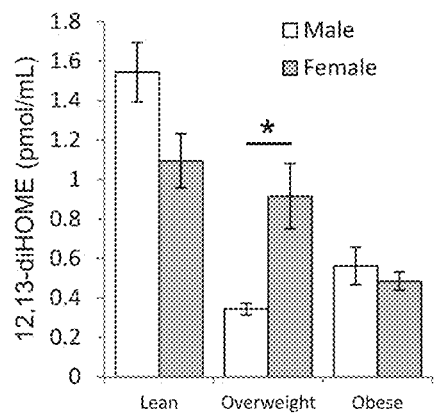
Figure 4L:
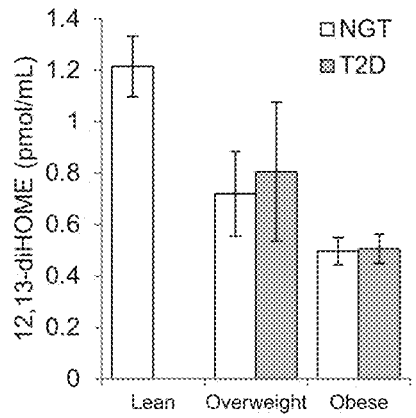

BAT activity and mass are both decreased with obesity (Townsend, K. L. & Tseng, Y. H., *Adipocyte.* 1, 13-24 (2012)). So to determine if 12,13-diHOME links to human obesity and its related metabolic disorders, 12,13-diHOME levels were measured in a cohort of 55 lean, overweight, and obese human subjects at room temperature. Importantly, significant negative associations were found between plasma levels of 12,13-diHOME and body mass index (BMI), insulin resistance (measured by HOMA-IR), fasting plasma insulin and glucose concentrations (FIGS. 2D-2E and FIGS. 4B, 4C, and 4J), although the correlation with hemoglobin A1c and c-reactive peptide was not as strong (FIGS. 4D-4E). Consistent with BMI, circulating triglycerides and leptin were also negatively correlated with plasma 12,13-diHOME levels (FIG. 2F and FIG. 4F). Intriguingly, circulating markers of liver function, such as alanine transaminase (ALAT) (FIG. 2G), aspartate transaminase (ASAT) (FIG. 3H), and gamma-glutamyl transpeptidase (gGT) (FIG. 4I), were inversely correlated with 12,13-diHOME levels. Cholesterol, on the other hand, did not correlate with circulating 12,13-diHOME concentration (FIGS. 2G-2H and FIG. 4G). In this particular cohort of subjects, circulating 12,13-diHOME was found to have no association with age, gender or diabetes (FIGS. 4A, 4K, and 4L).

Figure 5A:
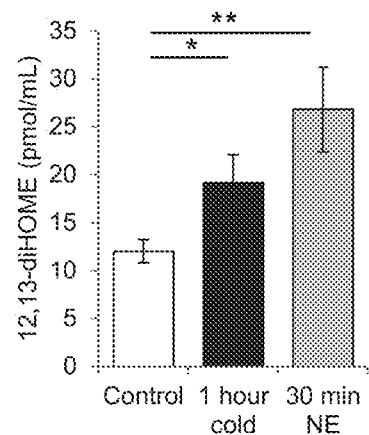
FIGS. 5A-5H depict that the biosynthetic pathway of 12,13-diHOME is selectively increased in BAT with cold in mice.
Figure 5B:
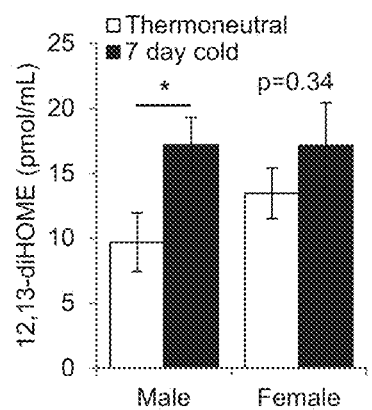
Figure 6A:
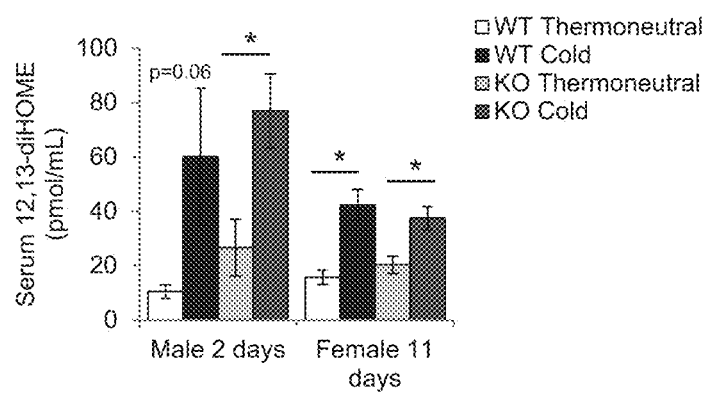
FIGS. 6A-6G depict 12,13-biosynthesis in cold activated adipose tissue.

Example 2. Biosynthetic Pathway of 12,13-diHOME is Selectively Increased in BAT with Cold in Mice To allow in-depth mechanistic studies, a cold exposure model was established using mice housed at either 30° C. thermoneutrality (minimal BAT activity) or 4° C. (maximal BAT activity) for various durations. Consistent with what was observed in humans, exposing mice to 4 C for 1 hour significantly increased circulating 12,13-diHOME (FIG. 5A). Interestingly, treatment of mice with norepineprine (NE) for 30 minutes, which mimics sympathetic activation, also induced 12,13-diHOME production, suggesting that 12,13-diHOME is a potential product induced by cold and sympathetic activation. Similar to acute cold challenge, one week of cold exposure also induced a pronounced increase in circulating 12,13-diHOME in male mice (FIG. 5B). In female mice, there was a trend for increased circulating 12,13-diHOME after one week, however, this increase did not reach statistical significance until after 11 days of cold exposure (FIG. 5B and FIG. 6A), which may be related to the reported sexual dimorphism of lipid profiles in mouse BAT (Hoene, M., et al., *Biochim. Biophys. Acta.* 1842, 1563-1570 (2014)).

Figure 5C:
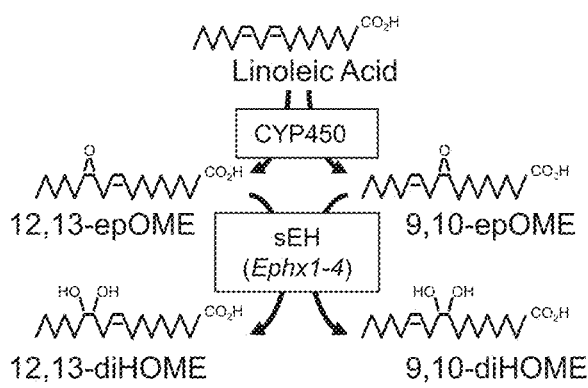
Figure 5D:
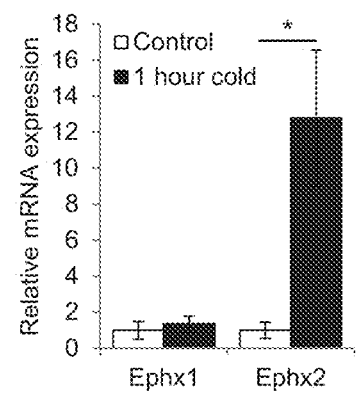
Figure 5E:
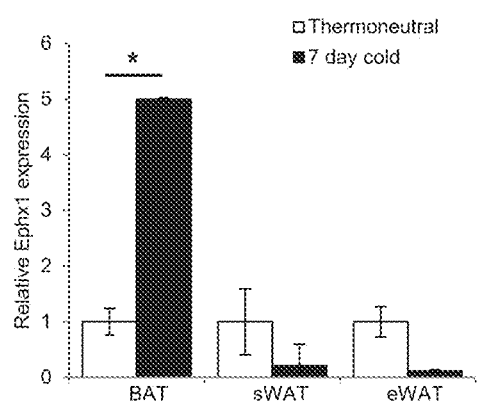
Figure 5F:
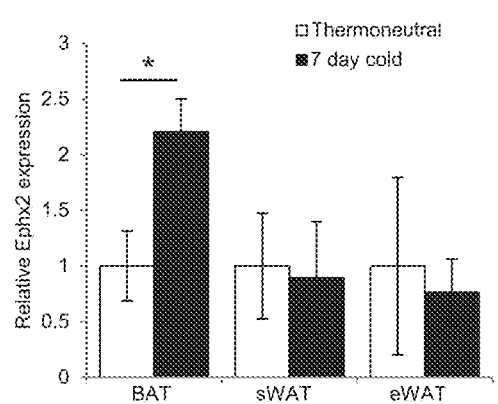
Figure 5G:
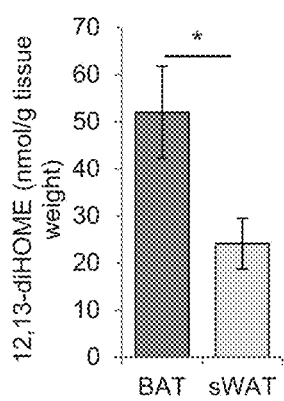
Figure 6B:
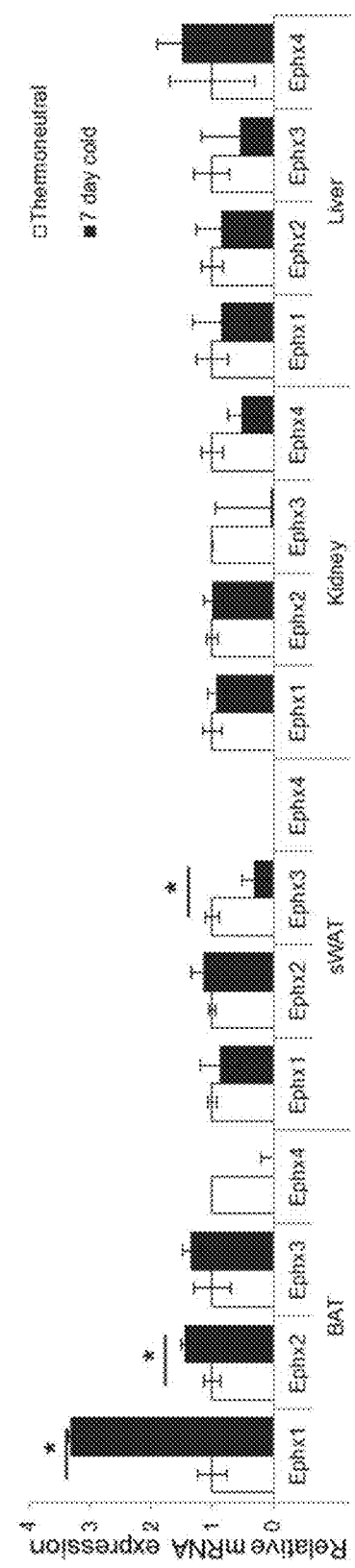
Figure 6C:
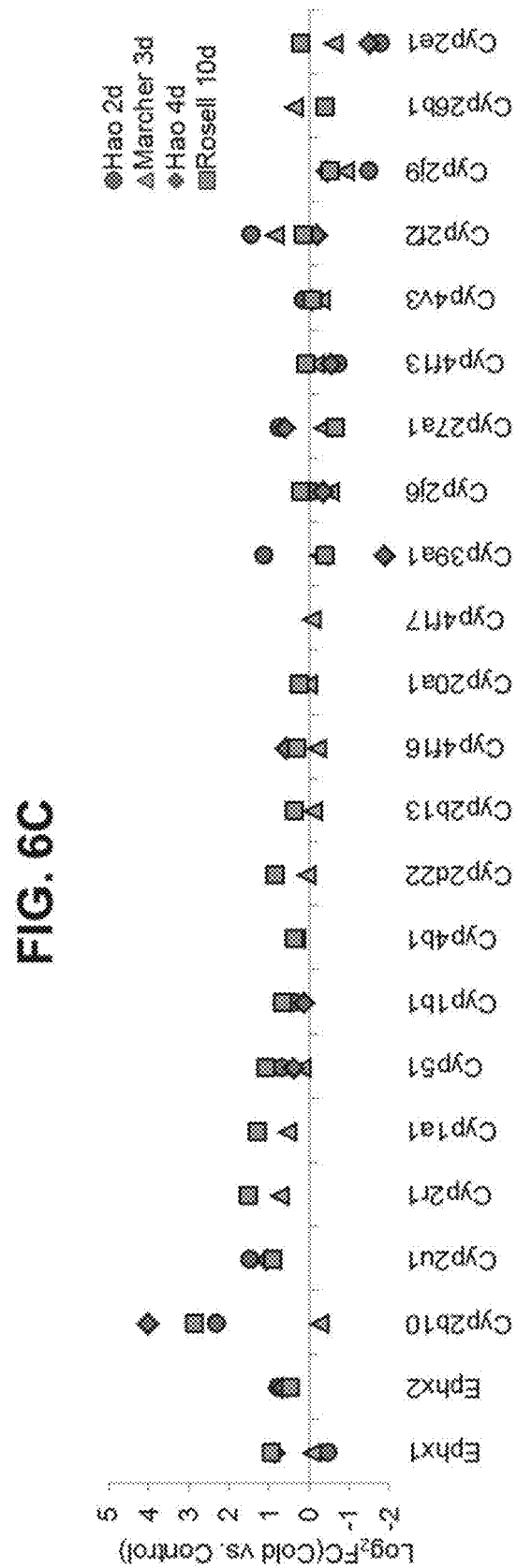
Figure 6D:
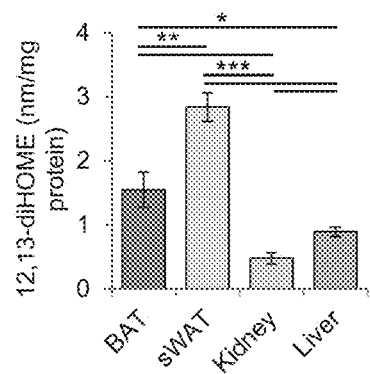

12,13-diHOME was originally identified in mice as a component of the neutrophil oxidative burst (Thompson, D. A. & Hammock, B. D., *J Biosci.* 32, 279-291 (2007)), but has not been previously linked to cold or BAT biology. Biosynthesis of 12,13-diHOME and its isoform 9,10-diHOME begins via formation of 12,13- or 9,10-epOME epoxides from linoleic acid by Cytochrome P450 (Cyp) oxidases, followed by hydrolysis catalyzed by soluble epoxide hydrolases (sEH) to form the diols 12,13-diHOME and 9,10-diHOME (FIG. 5C). Among the four sEH genes, Ephx1 and Ephx2 are the major isoforms expressed in adipose tissue (Su, A. I., et al., *Proc Natl. Acad Sci. U S. A* 101, 6062-6067 (2004)) and although Ephx2 null mice have decreased blood pressure (Sinal, C. J., et al., *J Biol Chem.* 275, 40504-40510 (2000)), thermogenic function has not been reported in Ephx1 (Miyata, M., et al., *J Biol Chem.* 274, 23963-23968 (1999)) or Ephx2 knockout mice. The present data demonstrate that acute cold exposure (i.e., 1 hour) induced a nearly 14-fold increase of Ephx2 in BAT (FIG. 5D). Chronic cold (e.g., 1 week) also significantly increased both Ephx1 (FIG. 5E) and Ephx2 (FIG. 5F) expression only in BAT but not other tissues where sEH is expressed (FIG. 6B). Meta-analysis of publically available datasets profiling gene expression in BAT from mice exposed to cold for different periods of time also consistently showed increased Ephx expression and differential regulation of several Cyp genes that may participate in this pathway ((Marcher, A. B., et al., *Cell Rep.* 13, 2000-2013 (2015); Hao, Q., et al., *Am J Physiol Endocrinol Metab.* 308, E380-392 (2015); Rosell, M., et al., *Am J Physiol Endocrinol Metab.* 306, E945-964 (2014)) in BAT (FIG. 6C). Further, high levels of 12,13-diHOME were detected in adipose tissue (FIG. 6D), and ex vivo experiments demonstrated that 12,13-diHOME secretion from BAT is higher than WAT (FIG. 5G).

Figure 5H:
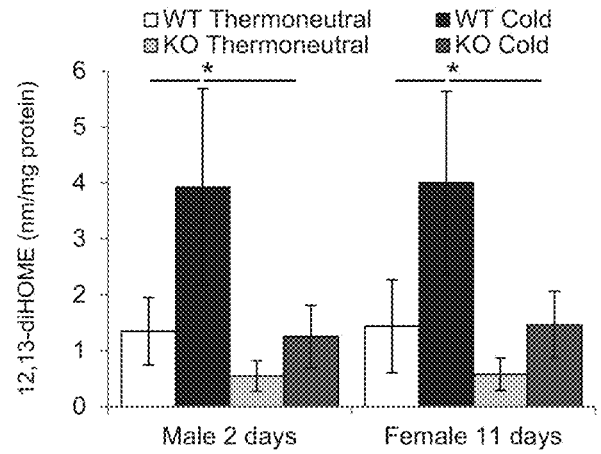
Figure 6E:
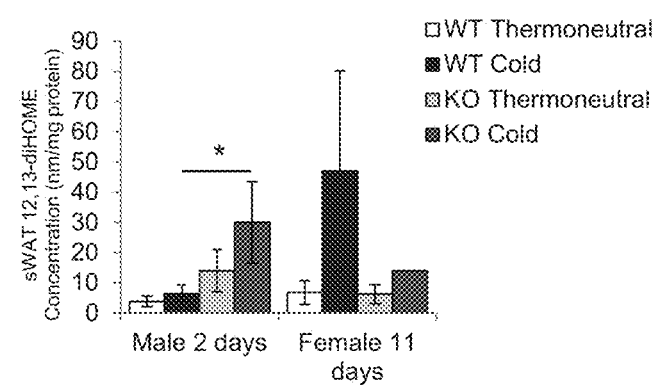
Figure 6F:
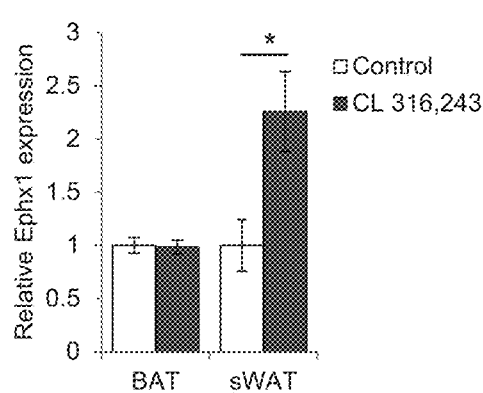
Figure 6G:
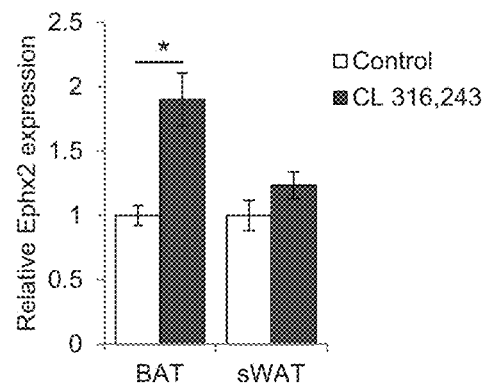

To further investigate whether BAT or WAT could be a possible source of 12,13-diHOME upon cold exposure, LC-MS/MS was used to measure 12,13-diHOME in adipose from wild-type and Myf5$^{cre}$BMPr1a$^{f/f}$ mice (KO), which display a severe defect in classical BAT development and a compensatory browning of sWAT (Schulz, T. J., et al., *Nature.* 495, 379-383 (2013)). Cold exposure increased 12,13-diHOME concentration in BAT from wild-type mice, yet, this effect was severely impaired in BAT from the KO mice (FIG. 5H). These data strongly suggest that BAT is a major source of increased circulating 12,13-diHOME after cold exposure, although circulating 12,13-diHOME in KO mice is not different from control animals (FIG. 6A), raising the possibility that beige adipocytes recruited in sWAT tissue of the KO mice might also be a potential source. Concordant with this, the present data revealed that 12,13-diHOME levels were elevated in sWAT from cold challenged male KO mice with enhanced beige adipogenesis compared to wild-type mice housed in cold for two days, while no effect was observed after 11 days in female mice (FIG. 6E). Interestingly, pharmacologic BAT activation using daily treatment with the 33-adrenergic agonist CL316,243 for 10 days increased Ephx2 expression in BAT and Ephx1 expression in sWAT (FIGS. 6F and 6G), suggesting that 12,13-diHOME can be produced by brown or beige fat in response to β-adrenergic stimulation. One challenge to understanding the flux of 12,13-diHOME in vivo is that this lipid can be both consumed in the diet and produced in the body, so further characterization of the biosynthetic pathway will require labeling 12,13-diHOME itself and warrants future studies.

Figure 7A:
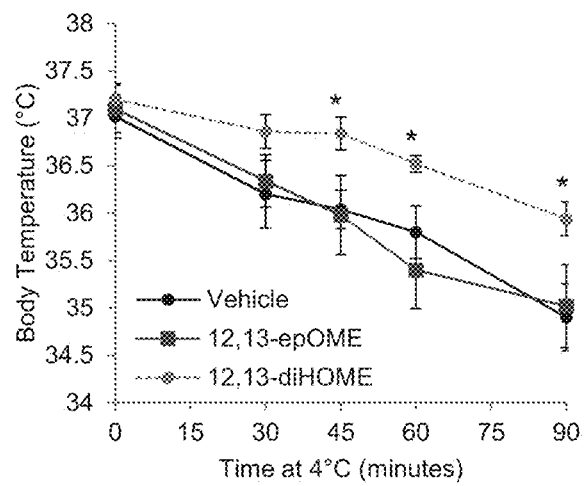
FIGS. 7A-7H depict that 12,13-diHOME enhances cold tolerance and facilitates fatty acid uptake into BAT.
Figure 7B:
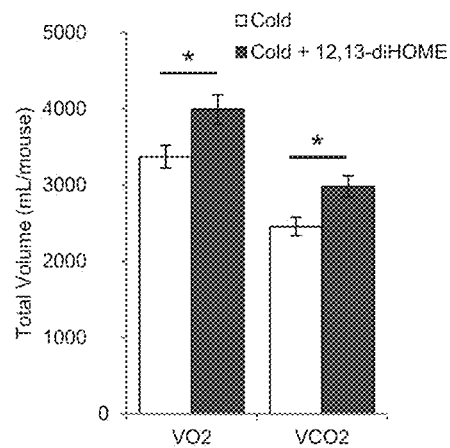
Figure 7C:
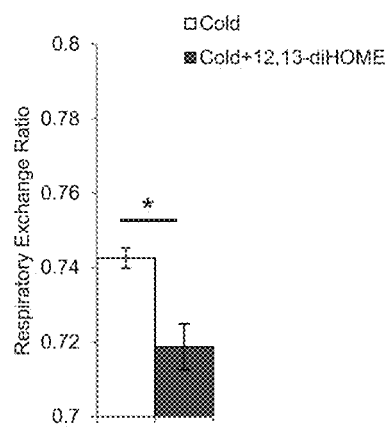
Figure 8A:
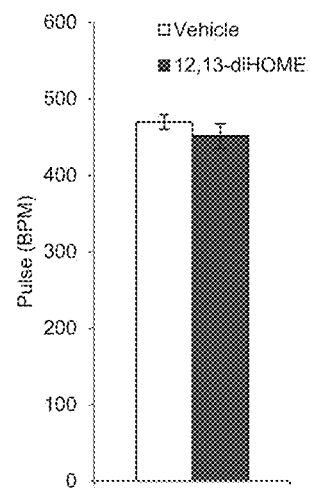
FIGS. 8A-8C depict physiologic effects of acute 12,13-diHOME treatment in mice.
Figure 8B:
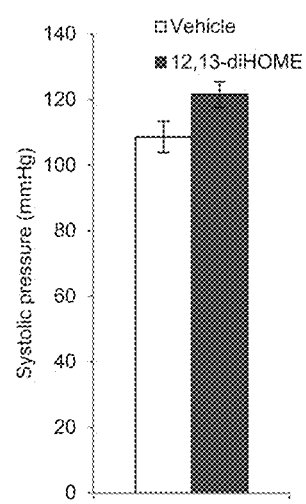
Figure 8C:
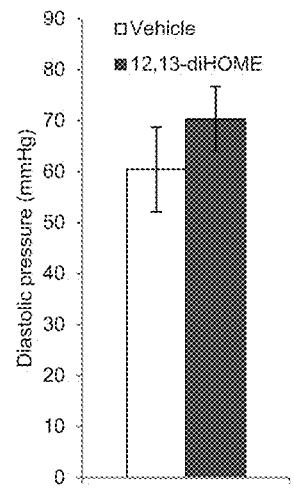

Example 3. 12,13-diHOME Enhances Cold Tolerance and Facilitates Fatty Acid (FA) Uptake into BAT in In Vivo Study To determine whether putative lipokines induced by cold can facilitate increased thermogenesis, mice were treated with either 12,13-diHOME or vehicle, and core body temperature was measured during an acute cold challenge. To minimize cytotoxic effects, the dosage of 1 µg/kg was used with a target concentration of 30-50 nM for in vivo administration to mimic the physiologic concentration after cold exposure. This dose is based on the measured circulating concentration of 12,13-diHOME at room temperature and after cold exposure, and is many hundred-folds lower than the reported concentration that causes lung mitochondrial dysfunction (Sisemore, M. F., et al., *Arch Biochem Biophys.* 392, 32-37 (2001)). Importantly, treatment with 12,13-diHOME protected mice from the decrease in body temperature during cold challenge compared to both vehicle-treated mice and mice injected with the precursor lipid 12,13-epOME (FIG. 7A). Interestingly, except for a very transient increase in diastolic pressure, 12,13-diHOME had no effect on blood pressure and pulse (FIGS. 8A-8C), suggesting that 12,13-diHOME possesses a therapeutic benefit over sympathomimetics for BAT activation by avoiding potential side effects (Redman, L. M., et al., *Journal of Clinical Endocrinology & Metabolism.* 92, 527-531 (2007)), such as tachycardia or hypertension. Consistent with these findings, 12,13-diHOME-treated animals displayed significant increases in oxygen consumption and carbon dioxide production in the cold (FIG. 7B). These changes resulted in a decrease in the respiratory exchange ratio (FIG. 7C), indicating increased lipid oxidation and further suggesting the effect of 12,13-diHOME on BAT metabolism is mediated, at least in part, through enhanced lipid metabolism.

Figure 7D:
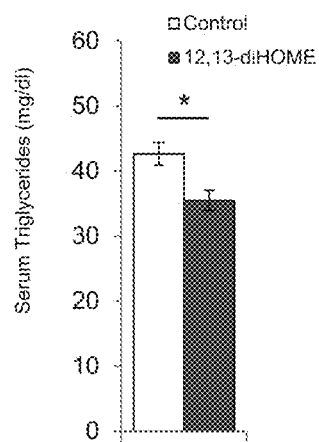
Figure 7E:
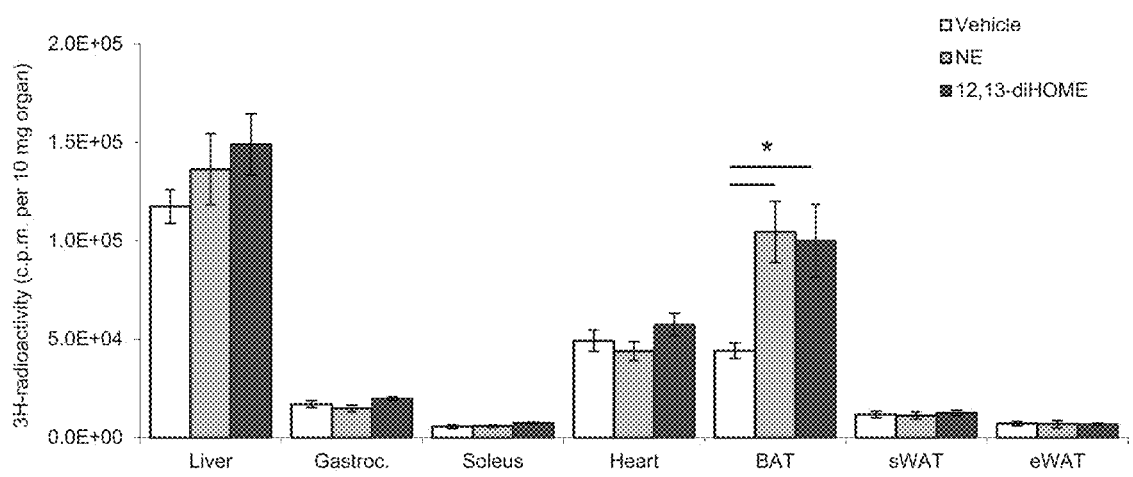
Figure 9A:
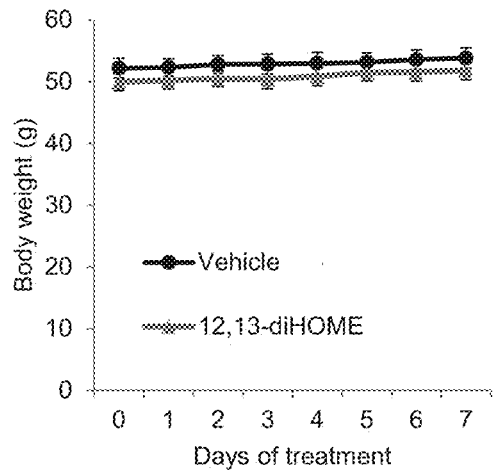
FIGS. 9A-9G depict physiologic effects of daily 12,13-diHOME injections.
Figure 9B:
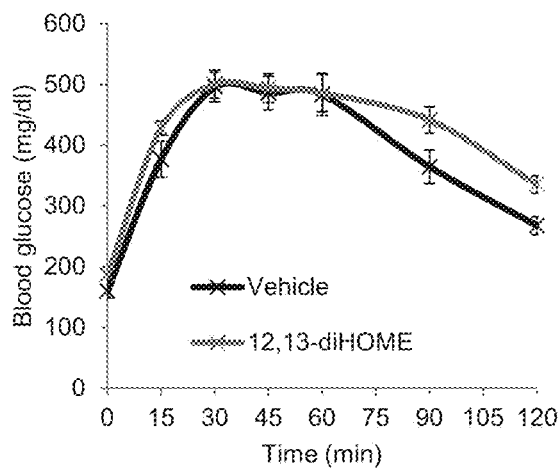
Figure 9C:
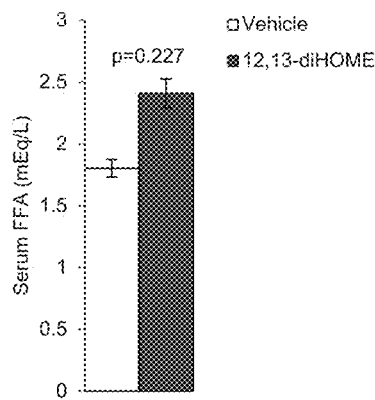
Figure 9D:
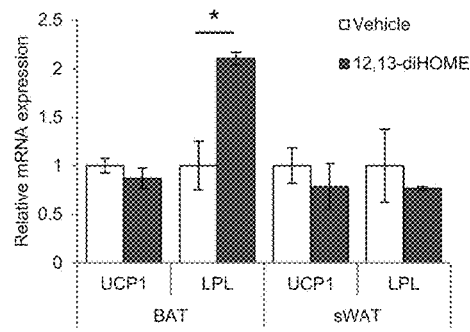
Figure 9E:
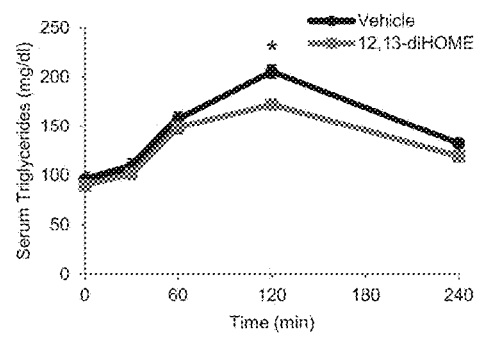
Figure 9F:
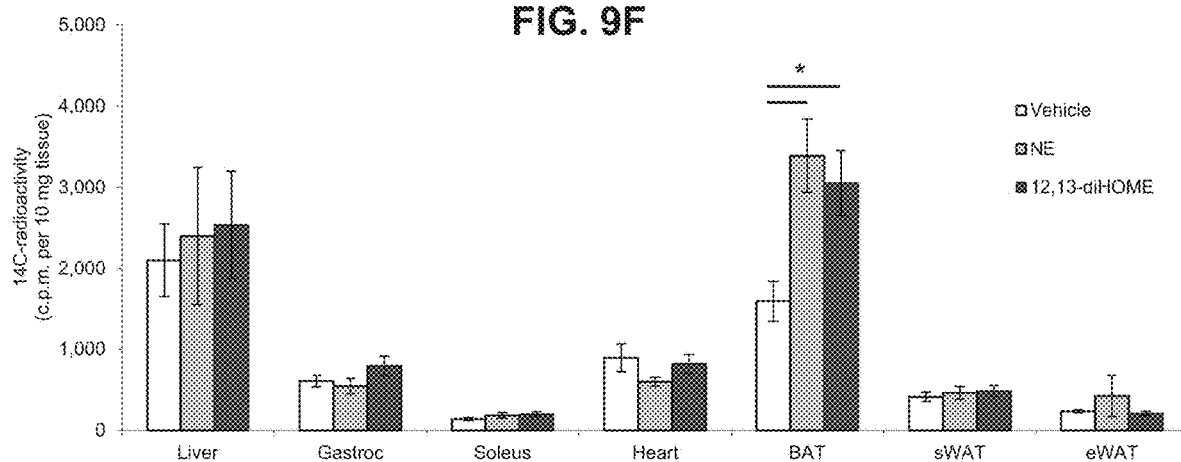
Figure 9G:
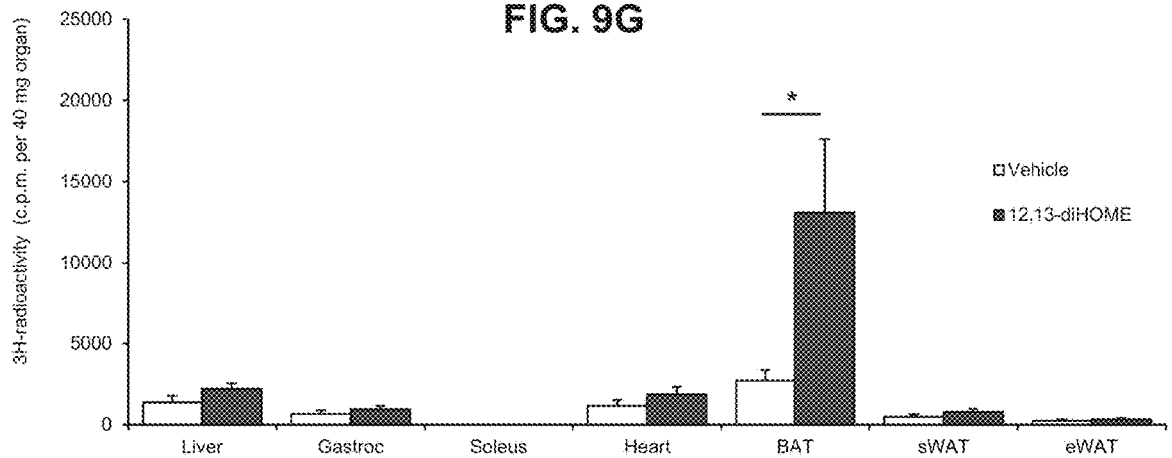

Example 4. In Vivo Administration of 12,13-diHOME in Obese Mice Reduced Circulating Triglyceride Levels To test therapeutic applications of 12,13-diHOME, diet-induced obese mice were treated with 12,13-diHOME daily for 2 weeks at 10 µg/kg body weight. Although no effect was seen on body weight, glucose tolerance, or circulating non-esterified FA (FIGS. 9A-9C), at this dose, 12,13-diHOME significantly decreased circulating triglyceride levels (FIG. 7D) and increased expression of lipoprotein lipase (LPL) in BAT, suggesting increased hydrolysis of triglycerides (Klingenspor, M., et al., *J Lipid Res.* 37, 1685-1695 (1996); Bartelt, A., et al., *Nat. Med.* 17, 200-205 (2011)) (FIG. 9D). The foregoing results, together with well-supported reports that activated BAT takes up large quantities of FA from circulating triglyceride-rich lipoproteins (Bartelt, A., et al., *Nat. Med.* 17, 200-205 (2011); Berbee, J. F., et al., *Nature Communications.* 6, 6356 (2015); Khedoe, P. P., et al., *J Lipid Res.* 56, 51-59 (2015); Schlein, C., et al., *Cell Metab.* 23, 441-453 (2016); Warner, A., et al., *Am J Physiol Endocrinol Metab*, ajpendo.00204.02016 (2016); Henkin, A. H., et al., *ACS Chem Biol.* 7, 1884-1891 (2012)), suggested testing the effects of 12,13-diHOME on FA uptake in vivo. Indeed, mice treated with 12,13-diHOME exhibited improved oral lipid tolerance (FIG. 9E) and a significant increase in FA (FIG. 7E) and glucose (FIG. 9F) uptake specifically into BAT, to a similar level achieved by NE. Since the principal source of FA in vivo is in the form of triglycerides packaged into lipoproteins, the foregoing data further demonstrated that 12,13-diHOME also enhanced BAT specific uptake of radiolabeled triglyceride delivered by oral gavage (FIG. 9G).

Figure 7F:
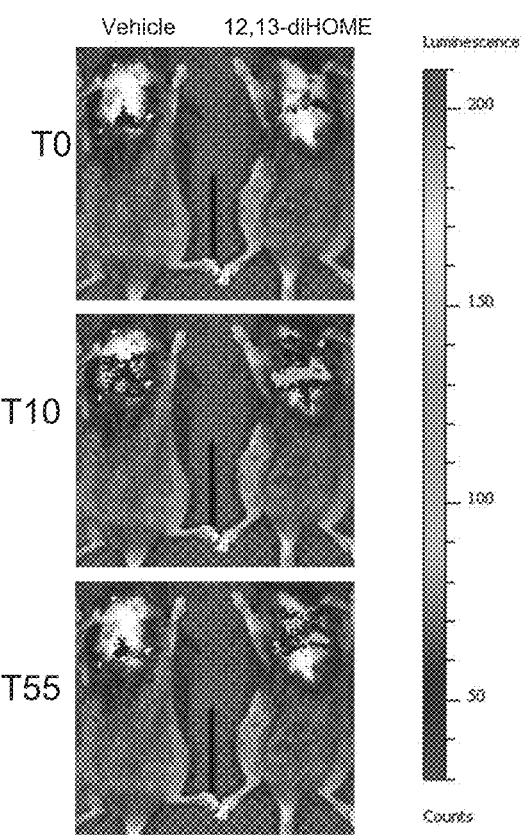
Figure 7G:
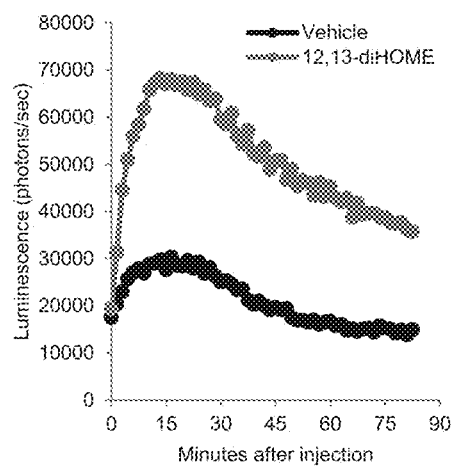
Figure 7H:
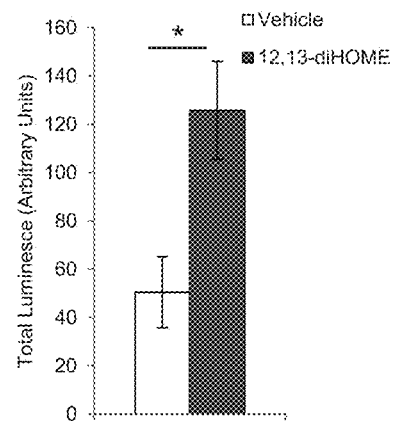

Given the fast and dynamic nature of FA uptake, 12,13-diHOME-stimulated fatty acid uptake was monitored in real time. Therefore, transgenic mice expressing firefly luciferase specifically in brown adipocytes (UCP1cre$^{+/-}$Rosa(stop)Luc$^{+/-}$) were generated. These mice were intravenously injected with FFA-SS-Luc, a fatty acid-luciferin conjugate that follows the uptake of natural FA and releases luciferin only after internalization (Henkin, A. H., et al., *ACS Chem Biol.* 7, 1884-1891 (2012)). In this model, luciferase is exclusively expressed in UCP1-expressing adipocytes. Therefore, the luciferin substrate can only be oxidized in these cells to release light to measure brown adipocyte FA uptake (FIG. 7F). Mice treated with 12,13-diHOME had a significantly increased luminescent signal in BAT compared to vehicle-treated animals that was both rapid and sustained over the course of the experiment (FIGS. 7G and 7H). Taken together, these data demonstrate a pro-thermogenic effect of 12,13-diHOME that is linked to acute BAT-specific FA uptake.

Figure 10A:
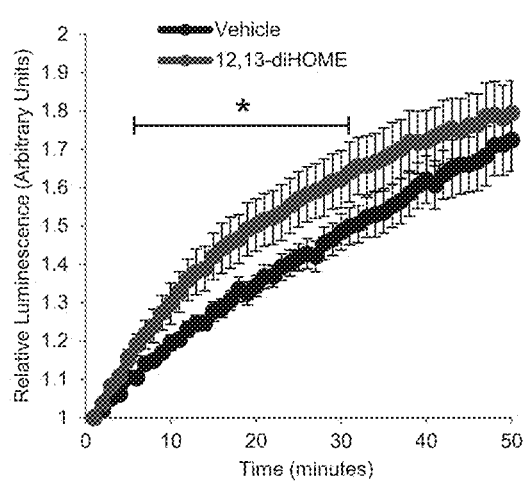
FIGS. 10A-10H depict that 12,13-diHOME promotes fatty acid uptake in vitro by activating the translocation and oligomerization of FA transporters.
Figure 10B:
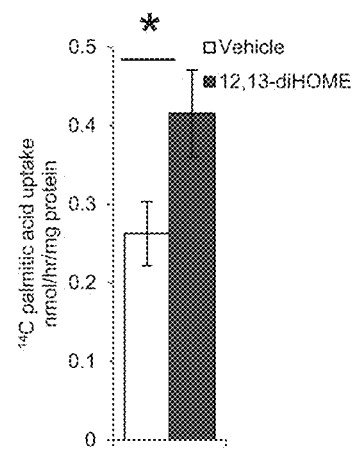
Figure 10C:
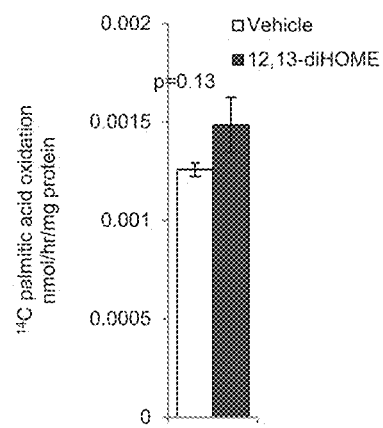
Figure 10D:
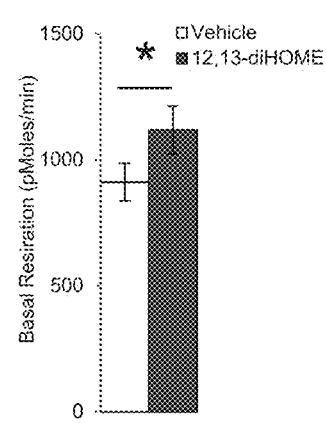
Figure 10E:
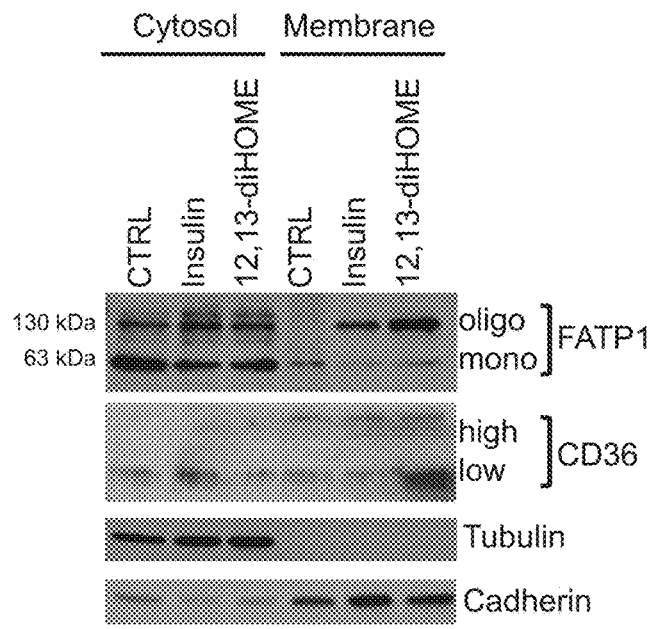
Figure 10F:
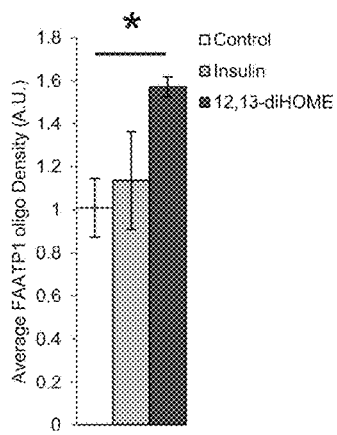
Figure 10G:
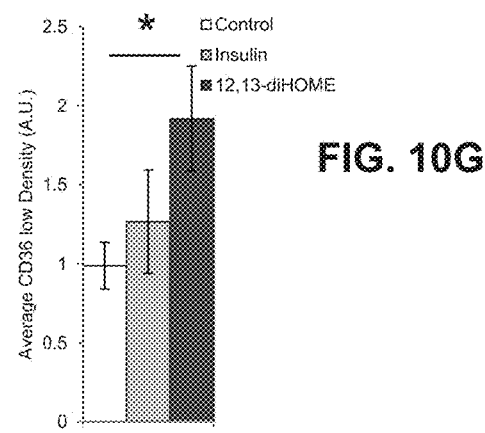

Example 5. 12,13-diHOME Promotes Fatty Acid Uptake In Vitro by Activating the Translocation and Oligomerization of FA Transporters To identify potential cell autonomous mechanisms for increased FA uptake in BAT, effects of 12,13-diHOME on brown adipocytes constitutively expressing luciferase in vitro, was tested. In agreement with the foregoing experiments in vivo, FFA-SS-Luc uptake in vitro was also significantly increased (FIG. 10A), while no additive effect of NE treatment was observed (data not shown), suggesting 12,13-diHOME might act downstream of NE. Similarly, 12,13-diHOME markedly increased radiolabeled FA uptake with a trend to increase FA oxidation (FIGS. 10B and 10C). As a result of consuming the FA fuel, basal respiration was significantly increased in 12,13-diHOME treated brown adipocytes (FIG. 10D), but there was no effect on maximal respiratory capacity or uncoupling, indicating the effect of 12,13-diHOME was primarily to increase metabolic flux and fuel consumption (data not shown). In adipocytes, FA uptake is mediated in part by a diverse family of fatty acid transport proteins including CD36 and FATP1, both of which are hormone-sensitive FA transporters (Schlein, C., et al., *Cell Metab.* 23, 441-453 (2016); Stahl, A., et al., *Dev. Cell.* 2, 477-488 (2002)) required for non-shivering thermogenesis in mice (Wu, Q., et al., *Diabetes.* 55, 3229-3237 (2006); Putri, M., et al., *Biochem Biophys Res Commun.* 457, 520-525 (2015)). Membrane translocation of both the low glycosylation form of CD36 (Schlein, C., et al., *Cell Metab.* 23, 441-453 (2016)) and oligomeric FATP1 (Richards, M. R., et al., *J Biol Chem.* 278, 10477-10483 (2003)) are robustly induced by 12,13-diHOME, consistent with increased fatty acid uptake (FIGS. 10E-10G).

Figure 10H:
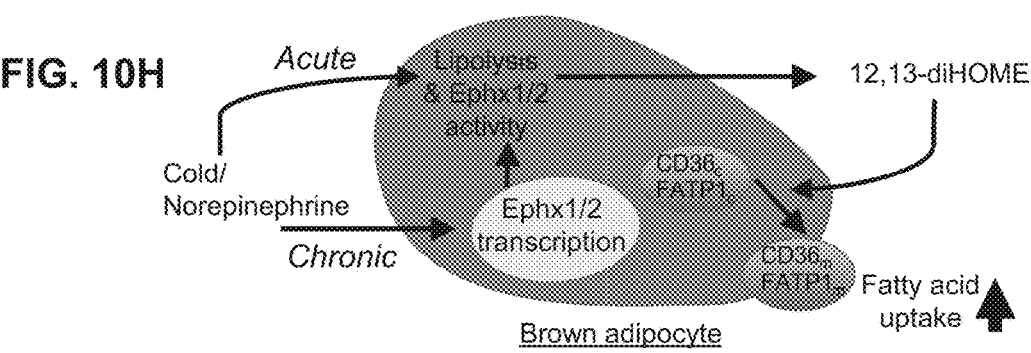

Taken together, these foregoing results suggest a model (FIG. 10H), wherein cold exposure activates NE-mediated lipolysis, providing FA substrates for the production of 12,13-diHOME in BAT tissue, ultimately leading to increased circulating levels of this lipokine. 12,13-diHOME acts, at least in part, via an autocrine/paracrine mechanism to activate fatty acid transporter translocation in brown adipocytes leading to increased FA uptake and triglyceride clearance, facilitating thermogenesis by providing fuel. Chronic cold exposure further increases gene expression of sEH, specifically in brown or beige adipocytes, providing a second mechanism whereby biosynthesis of 12,13-diHOME could be increased. Interestingly, even metabolically inert fatty acids are known to directly activate UCP1 (Shabalina, I. G., et al., *Archives of toxicology.* 90, 1117-1128 (2016)), and the direct effects of 12,13-diHOME on UCP1-mediated uncoupling require further investigation. The foregoing in vivo experiments, however, support a direct effect of 12,13-diHOME on FA uptake.

The foregoing model indicates that, 12,13-diHOME facilitates BAT thermogenic activity by selectively promoting fuel uptake, suggesting potential applications for treating hyperlipidemia. Indeed, the present data demonstrate that acute 12,13-diHOME treatment protected mice from cold challenge, and chronic treatment (i.e., one week) of obese mice with 12,13-diHOME resulted in a significant reduction of circulating triglyceride without alteration of body weight. These data point out a complex fuel consumption and refueling process that impact energy balance during cold exposure and presumably upon 12,13-diHOME treatment. In cold conditions, the fatty acids generated by lipolysis in brown adipocytes serve as both fuel to be oxidized for thermoregulation, as well as substrates for biosynthesis of 12,13-diHOME. Since 12,13-diHOME activates fatty acid uptake, consumption of cellular fuel is coupled to a potent and specific refueling signal.

We claim:

1. A method of detecting a 12,13-diHOME level in a human subject to determine whether the human subject has brown adipose tissue activation, said method comprising
   a) obtaining a plasma sample from the human subject;
   b) detecting a 12,13-diHOME level in the plasma sample; and
   c) comparing the 12,13-diHOME level with a known baseline of plasma 12,13-diHOME level,
   such that it is determined whether the human subject has brown adipose tissue activation.

2. The method of claim 1, wherein the 12,13-diHOME levels in the plasma sample are detected using mass spectrometry.

3. The method of claim 1, wherein the known baseline level of plasma 12,13-diHOME level is 0.2 pmol/mL.

4. A method of determining whether a human subject has brown adipose tissue (BAT) activation, said method comprising determining the level of 12,13-diHOME in a plasma sample from the human subject, wherein a plasma 12,13-diHOME level of 0.2 pmol/mL or greater indicates BAT activation.

5. The method of claim 4, wherein the level of 12,13-diHOME is determined using mass spectrometry.

6. The method of claim 1, wherein the subject has a metabolic disorder or heart disease.

7. The method of claim 6, wherein the metabolic disorder is selected from the group consisting of hyperlipidemia, insulin resistance, metabolic syndrome, obesity, and diabetes.

8. The method of claim 4, wherein the human subject has at least one of the following characteristics
   a) a plasma alanine transaminase (ALAT) level greater than 0.6 μkat/l;
   b) a Body Mass Index (BMI) of 30 or more;
   c) a Homeostatic Model Assessment of Insulin Resistance (HOMA-IR) score of 1.9 or more;
   d) a plasma triglyceride level greater than 1.7 mmol/l;
   e) a plasma aspartate transaminase (ASAT) level of greater than 0.3 μkat/l for a male subject or a plasma ASAT level of greater than 0.6 μkat/l for a female subject;
   f) a plasma leptin level of 40 ng/ml or more; or
   g) a plasma gGT level of 0.9 μkat/l or greater for a male subject or a plasma gGT level of 0.6 μkat/l or greater for a female subject.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tttgggcatc accacgaaaa                                              20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggacaccctc cagaaagcga                                              20

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggagacctta ccacttgaag atg                                          23

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gcccggaacc tatctatcct ct                                           22

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 5
accactcatg gatgaaagct aca                                              23

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tcaggtagat tggctccaca g                                                21

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
cagtggactc cgatagcacg                                                  20

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tgggacgact acagagccg                                                   19

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tccctggtgt acggctactg                                                  20

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
atcttaaccc ggagtccttg a                                                21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 11
aggcttccag taccattagg t                                        21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ctgagtgagg caaagctgat tt                                       22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gcccagcaac attatccagt                                          20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggtcagactt cctgctacgc                                          20
```